United States Patent
Darekar et al.

(10) Patent No.: US 12,383,395 B2
(45) Date of Patent: Aug. 12, 2025

(54) SKIRT-REINFORCEMENT MEMBERS FOR PROSTHETIC VALVE DEVICES

(71) Applicant: Medtronic, Inc., Minneapolis, MN (US)

(72) Inventors: Yogesh Darekar, Irvine, CA (US); Brenda McIntire, Walnut Creek, CA (US); Eric Pierce, Mission Viejo, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 872 days.

(21) Appl. No.: 17/533,332

(22) Filed: Nov. 23, 2021

(65) Prior Publication Data

US 2022/0192823 A1    Jun. 23, 2022

Related U.S. Application Data

(60) Provisional application No. 63/129,166, filed on Dec. 22, 2020.

(51) Int. Cl.
*A61F 2/24*    (2006.01)

(52) U.S. Cl.
CPC .......... *A61F 2/2409* (2013.01); *A61F 2/2418* (2013.01); *A61F 2220/0075* (2013.01);
(Continued)

(58) Field of Classification Search
CPC ........ A61F 2/24; A61F 2/2409; A61F 2/2418; A61F 2/2457; A61F 2/2412;
(Continued)

(56) References Cited

U.S. PATENT DOCUMENTS

| | | |
|---|---|---|
| 6,805,706 B2 | 10/2004 | Solovay et al. |
| 7,993,394 B2 | 8/2011 | Hariton et al. |

(Continued)

FOREIGN PATENT DOCUMENTS

| | | |
|---|---|---|
| EP | 3503846 A1 | 7/2019 |
| WO | 2018039543 A1 | 3/2018 |
| WO | 2019/086958 A1 | 5/2019 |

OTHER PUBLICATIONS

International Search Report and Written Opinion issued Apr. 7, 2022 in Intl Appl. No. PCT/US2021/063499.

(Continued)

*Primary Examiner* — Seema Mathew
(74) *Attorney, Agent, or Firm* — MEDLER FERRO WOODHOUSE & MILLS PLLC

(57) ABSTRACT

A prosthesis includes a frame and a skirt coupled to a surface of the frame. The skirt extends over at least one side opening of a plurality of side openings of the frame. The prosthesis also includes a skirt-reinforcement member that spans the at least one side opening from a first crown or strut edge defining the at least one side opening to a second crown or strut edge defining the at least one side opening. The skirt-reinforcement member has a first end, a second end, and a length therebetween. The first end of the skirt-reinforcement member is attached to the first crown or strut edge and the second end of the skirt-reinforcement member is attached to the second crown or strut edge. The skirt-reinforcement member is attached to the skirt along an unsupported portion of the skirt that spans the at least one side opening.

20 Claims, 18 Drawing Sheets

(52) U.S. Cl.
CPC . *A61F 2230/0067* (2013.01); *A61F 2250/001* (2013.01); *A61F 2250/0039* (2013.01)

(58) Field of Classification Search
CPC .... A61F 2250/0063; A61F 2/852; A61F 2/82; A61F 2/2442; A61F 2/2454
See application file for complete search history.

(56) References Cited

U.S. PATENT DOCUMENTS

| | | | |
|---|---|---|---|
| 9,034,032 B2 | 5/2015 | McLean et al. | |
| 9,681,951 B2 | 6/2017 | Ratz et al. | |
| 10,195,025 B2 | 2/2019 | Levi et al. | |
| 11,622,853 B1* | 4/2023 | Quill | A61F 2/2412 623/2.12 |
| 2010/0036484 A1* | 2/2010 | Hariton | A61F 2/2412 623/2.18 |
| 2010/0185277 A1* | 7/2010 | Braido | A61F 2/89 623/2.37 |
| 2012/0296418 A1* | 11/2012 | Bonyuet | A61F 2/2415 623/2.18 |
| 2013/0150956 A1* | 6/2013 | Yohanan | A61F 2/2433 623/2.14 |
| 2013/0316642 A1* | 11/2013 | Newham | H04W 52/0206 455/67.11 |
| 2015/0173899 A1* | 6/2015 | Braido | A61F 2/2445 623/2.38 |
| 2015/0209141 A1 | 7/2015 | Braido et al. | |
| 2015/0230923 A1* | 8/2015 | Levi | A61F 2/2418 623/2.36 |
| 2016/0045309 A1* | 2/2016 | Valdez | A61F 2/2412 623/2.38 |
| 2018/0256377 A1 | 9/2018 | Shalev | |
| 2018/0263765 A1 | 9/2018 | Flaction | |
| 2019/0076244 A1 | 3/2019 | Yohanan et al. | |
| 2019/0091014 A1 | 3/2019 | Arcaro et al. | |
| 2019/0231514 A1 | 8/2019 | Arbefeuille | |
| 2019/0262129 A1 | 8/2019 | Cooper et al. | |
| 2021/0045868 A1* | 2/2021 | Reimer | B33Y 80/00 |
| 2022/0175521 A1* | 6/2022 | Baldwin | A61F 2/2418 |
| 2022/0192823 A1* | 6/2022 | Darekar | A61F 2/2409 |
| 2022/0249227 A1* | 8/2022 | Nir | A61F 2/2415 |
| 2022/0338981 A1* | 10/2022 | Alkhatib | A61F 2/2418 |
| 2023/0143332 A1* | 5/2023 | Levi | A61F 2/2412 623/2.18 |
| 2023/0149157 A1* | 5/2023 | Licht | A61F 2/2418 623/2.11 |
| 2023/0240840 A1* | 8/2023 | Ben Zaken | A61F 2/2418 |
| 2023/0320848 A1* | 10/2023 | Morin | A61F 2/2418 623/2.17 |
| 2024/0041594 A1* | 2/2024 | Eidenschink | A61F 2/2415 |
| 2024/0180694 A1* | 6/2024 | Loughnane | A61F 2/2418 |
| 2024/0216131 A1* | 7/2024 | Levi | A61F 2/2418 |
| 2024/0382307 A1* | 11/2024 | Levi | A61F 2/2418 |
| 2025/0000644 A1* | 1/2025 | Nir | A61F 2/2418 |
| 2025/0009503 A1* | 1/2025 | Axelrod | A61F 2/2418 |
| 2025/0064584 A1* | 2/2025 | Bukin | A61F 2/2418 |
| 2025/0090311 A1* | 3/2025 | Gurovich | A61L 27/18 |
| 2025/0107892 A1* | 4/2025 | Hauser | A61F 2/2418 |
| 2025/0114192 A1* | 4/2025 | Darekar | A61F 2/2418 |

OTHER PUBLICATIONS

Communication pursuant to Article 94(3) EPC issued Jul. 25, 2024 in EP Appl. No. 21 841 124.7.

* cited by examiner

SKIRT-REINFORCEMENT MEMBERS FOR PROSTHETIC VALVE DEVICES

CROSS-REFERENCE TO RELATED APPLICATIONS

This application claims the benefit of U.S. Provisional Patent Application Ser. No. 63/129,166, filed Dec. 22, 2020, which is hereby incorporated by reference in its entirety for all purposes.

FIELD

The present technology is generally related to prosthetic valve devices, and in particular is directed to prosthetic valve devices including a skirt.

BACKGROUND

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs into systemic circulation. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The valve leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses are delivered in a radially compressed or crimped configuration so that the heart valve prosthesis can be advanced through the patient's vasculature. Once positioned at the treatment site, the heart valve prosthesis is expanded to engage tissue at the diseased heart valve region to, for instance, hold the heart valve prosthesis in position.

The present disclosure relates to improvements in a heart valve prosthesis to ensure that the heart valve prosthesis has a low profile for transcatheter delivery through a patient's vasculature.

SUMMARY

According to a first embodiment hereof, the present disclosure provides a prosthesis having a radially expanded configuration and a radially compressed configuration. The prosthesis includes a frame including a plurality of crowns and a plurality of struts with each crown being formed between a pair of opposing struts. A plurality of side openings is defined by edges of the plurality of crowns and the plurality of struts. The prosthesis also includes a skirt coupled to a surface of the frame. The skirt extends over at least one side opening of the plurality of side openings of the frame. The prosthesis also includes a skirt-reinforcement member that spans the at least one side opening from a first crown or strut edge defining the at least one side opening to a second crown or strut edge defining the at least one side opening. The skirt-reinforcement member has a first end, a second end, and a length therebetween. The first end of the skirt-reinforcement member is attached to the first crown or strut edge and the second end of the skirt-reinforcement member is attached to the second crown or strut edge. The skirt-reinforcement member is attached to the skirt along an unsupported portion of the skirt that spans the at least one side opening.

In an aspect of the first embodiment, and in combination with any other aspects herein, the disclosure provides that the skirt-reinforcement member includes a suture forming a plurality of stitches.

In an aspect of the first embodiment, and in combination with any other aspects herein, the disclosure provides that the skirt-reinforcement member includes tissue.

In an aspect of the first embodiment, and in combination with any other aspects herein, the disclosure provides that the skirt-reinforcement member includes fabric.

In an aspect of the first embodiment, and in combination with any other aspects herein, the disclosure provides that the at least one side opening is substantially diamond-shaped. In an embodiment, each side opening of the plurality of side openings is substantially diamond-shaped. In an embodiment, an end of the frame includes a row of side openings around a circumference of the frame, the row including between six and nine side openings.

In an aspect of the first embodiment, and in combination with any other aspects herein, the disclosure provides that the first end of the skirt-reinforcement member is offset from the second end of the skirt-reinforcement member such that the skirt-reinforcement member is angled relative to an axis of the frame.

In an aspect of the first embodiment, and in combination with any other aspects herein, the disclosure provides that the first end of the skirt-reinforcement member is aligned with the second end of the skirt-reinforcement member such that the skirt-reinforcement member extends substantially perpendicular relative to an axis of the frame. In an embodiment, the at least one side opening includes a maximum width and the skirt-reinforcement member spans across the at least one side opening at the maximum width. In an embodiment, the frame includes a plurality of nodes, each node being a region where two of the plurality of crowns of the frame meet, and the skirt-reinforcement member spans across the at least one side opening from one node to another node.

In an aspect of the first embodiment, and in combination with any other aspects herein, the disclosure provides that the frame includes a row of side openings around a circumference of the frame and a skirt-reinforcement member spans each side opening of the row of side openings around the circumference of the frame.

In an aspect of the first embodiment, and in combination with any other aspects herein, the disclosure provides that the frame is an inner frame and the prosthesis further comprises an outer frame coupled to the inner frame, the outer frame having a greater diameter than the inner frame.

In an aspect of the first embodiment, and in combination with any other aspects herein, the disclosure provides that the prosthesis is a heart-valve prosthesis and the prosthesis further comprises a prosthetic valve component disposed within and secured to the frame, the prosthetic valve being configured to block blood flow in one direction to regulate blood flow through a central lumen of the frame. In an embodiment, the heart-valve prosthesis is configured for placement within a mitral valve in situ.

According to a second embodiment hereof, the present disclosure provides a prosthesis having a radially expanded configuration and a radially compressed configuration. The prosthesis includes a frame including a plurality of crowns and a plurality of struts with each crown being formed between a pair of opposing struts. A plurality of side openings is defined by edges of the plurality of crowns and the plurality of struts. The prosthesis also includes a skirt coupled to a surface of the frame. The skirt extends over at least one side opening of the plurality of side openings of the frame. The prosthesis also includes a skirt-reinforcement member that circumscribes an outer surface of the frame. A diameter of the skirt-reinforcement member is approximately the same as a diameter of the frame when the prosthesis is in the radially expanded configuration. The skirt-reinforcement member is attached to the skirt along an unsupported portion of the skirt that spans the at least one side opening of the plurality of side openings of the frame and the skirt-reinforcement member is not directly attached to the frame.

In an aspect of the second embodiment, and in combination with any other aspects herein, the disclosure provides that the skirt-reinforcement member is a ring of an elastic material.

In an aspect of the second embodiment, and in combination with any other aspects herein, the disclosure provides that the at least one side opening of the plurality of side openings is substantially diamond-shaped and is defined by at least two struts. In an embodiment, each side opening of the plurality of side openings is substantially diamond-shaped and is defined by at least four struts. In an embodiment, an end of the frame includes a row of side openings around a circumference of the frame, the row including between six and nine side openings.

In an aspect of the second embodiment, and in combination with any other aspects herein, the disclosure provides that the frame is an inner frame and the prosthesis further comprises an outer frame coupled to the inner frame, the outer frame having a greater diameter than the inner frame.

In an aspect of the second embodiment, and in combination with any other aspects herein, the disclosure provides that the prosthesis is a heart-valve prosthesis and the prosthesis further comprises a prosthetic valve component disposed within and secured to the frame, the prosthetic valve being configured to block blood flow in one direction to regulate blood flow through a central lumen of the frame. In an embodiment, the heart-valve prosthesis is configured for placement within a mitral valve in situ.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Figure 1:
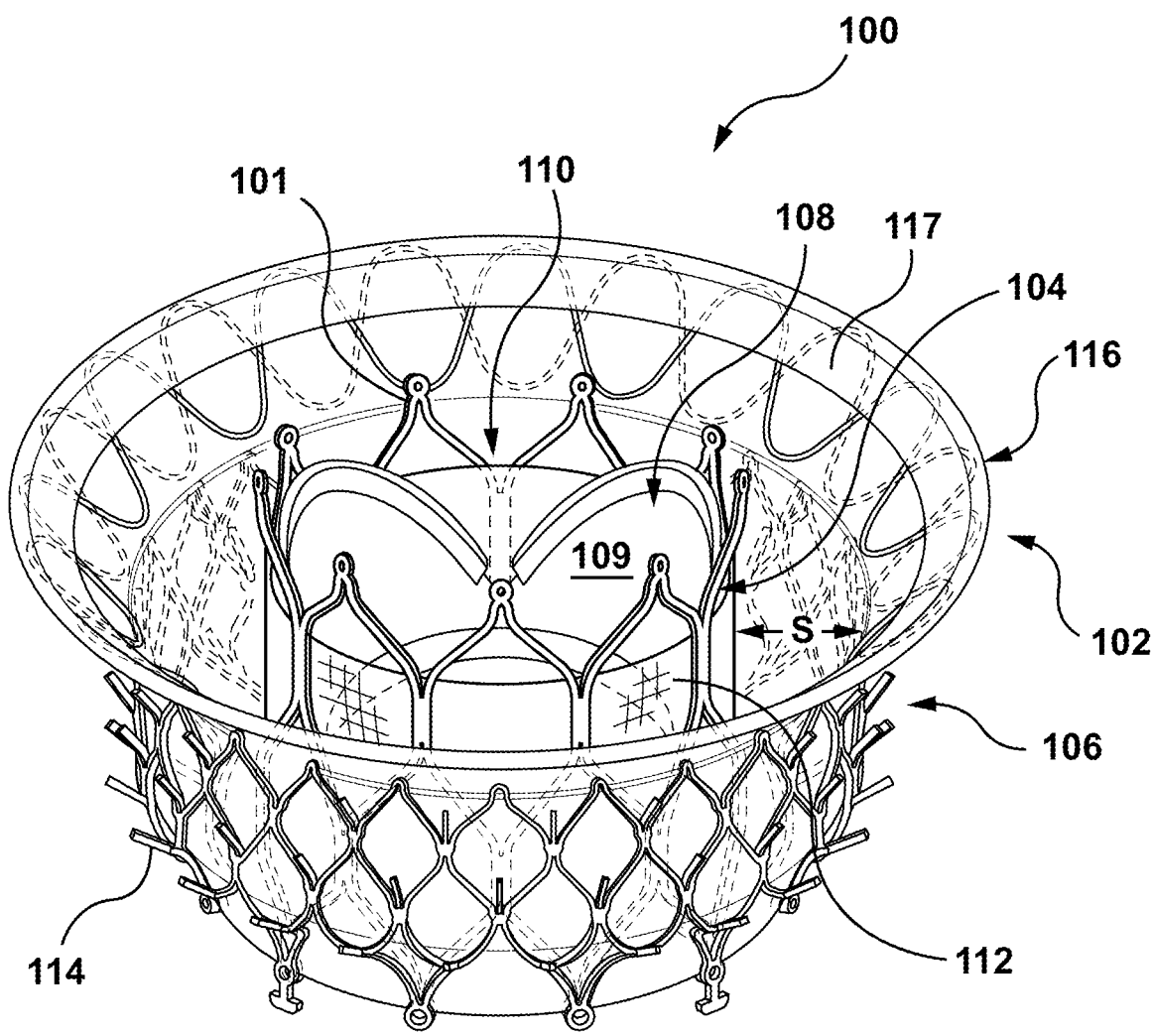
FIG. 1 depicts a perspective view of a transcatheter heart valve prosthesis in accordance with an aspect of the disclosure.

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a transcatheter heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

Embodiments hereof relate to a skirt-reinforcement member for supporting or reinforcement a skirt that spans across a side opening of a stent or frame of a valve prosthesis. The skirt-reinforcement member provides the valve prosthesis with a reinforced composite skirt having long-lasting durability and superior implant performance. In addition, as will be explained in more detail herein, the skirt-reinforcement member is configured to prevent billowing of the skirt material that spans across the side opening of the frame of the valve prosthesis, as such billowing may undesirably result in contact between the skirt and the leaflets of the valve prosthesis after the valve prosthesis is deployed in situ. If the leaflets of the valve prosthesis contact the skirt during opening and closing in situ, such contact may cause early leaflet tissue abrasion as well as early skirt abrasion due to the undesired billowing of the skirt. Additionally, the greater relative motion between the skirt and the frame may further induce early skirt abrasion. Early leaflet tissue abrasion and/or early skirt abrasion has a negative impact on the long-term durability of the valve prosthesis. The skirt-reinforcement members disclosed herein reinforce the material of the skirt that spans across the side opening of the frame of the valve prosthesis to limit the radial motion or billowing of the skirt material, thereby minimizing risk of damage to both the skirt and the leaflets.

FIGS. 1-6 illustrate a transcatheter heart valve prosthesis 100 that may be utilized with embodiments of skirt-reinforcement members described herein. The heart valve prosthesis 100 is illustrated herein in order to facilitate description of the present invention. The following description of the transcatheter heart valve prosthesis 100 is merely exemplary in nature and is not intended to limit the invention or the application and uses of the invention. It is understood that any number of alternate heart valve prostheses can be used with the skirt-reinforcement members described herein. Other non-limiting examples of transcatheter heart valve prostheses that can be used with the skirt-reinforcement members described herein are described in U.S. application Ser. No. 16/853,851 to McVeigh et al., U.S. Pat. No. 9,034,032 to McLean et al. and International Patent Application No. PCT/US2014/029549 to McLean et al, U.S. Patent Application Publication No. 2012/0101572 to Kovalsky et al., U.S. Patent Application Publication No. 2012/0035722 to Tuval, U.S. Patent Application Publication No. 2006/0265056 to Nguyen et al., U.S. Patent Application Publication No. 2007/05409266 to Birdsall, and U.S. Patent Application Publication No. 2007/05409269 to Dolan et al., each of which is incorporated by reference herein in its entirety. Although the transcatheter heart valve prosthesis 100 is a heart valve prosthesis configured for placement within a mitral heart valve, embodiments of skirt-reinforcement members described herein may be utilized with any valve prosthesis having a skirt. For example, embodiments of skirt-reinforcement members described herein may be utilized with a transcatheter heart valve configured for placement within a pulmonary, aortic, mitral, or tricuspid valve, or may be utilized with a transcatheter valve prosthesis configured for placement within a venous valve or within other body passageways where it is deemed useful. There is no intention to be bound by any expressed or implied theory presented in the preceding technical field, background, brief summary or the following detailed description. In addition, embodiments of skirt-reinforcement members described herein may be utilized with any stent or frame having a skirt for which reinforcement thereof is desirable to limit billowing, and it is not required that the stent or frame include a prosthetic valve component disposed therein.

A perspective view of the transcatheter heart valve prosthesis 100 in accordance with an aspect of the disclosure is shown in FIG. 1. The transcatheter heart valve prosthesis 100 is configured to be radially compressed into a reduced-diameter crimped configuration for delivery within a vasculature (not shown) and to return to an expanded, deployed configuration, as shown in FIG. 1. Stated another way, the transcatheter heart valve prosthesis 100 has a crimped configuration for delivery within a vasculature and an expanded configuration for deployment within a native heart valve. In accordance with embodiments hereof, when in the crimped configuration, the transcatheter heart valve prosthesis 100 has a low profile suitable for delivery to and deployment within a native heart valve via a suitable delivery catheter that may be tracked to the deployment site of the native heart valve of a heart via any one of a transseptal, retrograde, or transapical approach. The transcatheter heart valve prosthesis 100 includes a stent or frame 102 and a prosthetic valve component 108 including at least one leaflet disposed within and secured to the frame 102.

Any portion of the frame 102 described herein as an element of a heart valve prothesis 100 may be made from any number of suitable biocompatible materials, e.g., stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluoroethylene (PTFE), or any number of other materials or combination of materials. A suitable biocompatible material would be selected to provide the transcatheter heart valve prosthesis 100 to be configured to be compressed into a reduced-diameter crimped configuration for transcatheter delivery to a native valve, whereby release from a delivery catheter returns the prosthesis to an expanded, deployed configuration.

In an aspect of the disclosure, the frame 102 of the transcatheter heart valve prosthesis 100 includes a valve support 104 at least partially surrounded by and coupled to an anchor element 106. The valve support 104 is a tubular stent-like or frame structure that defines a central lumen 110 from an inflow end 101 of the valve support 104 to an outflow end 103 of the valve support 104. The valve support 104 is configured to support the prosthetic valve component 108 therein, which will be described in more detail below. In an embodiment, the valve support 104 has a substantially cylindrical shape in which the outflow end 103 of the valve support 104 has a diameter that is substantially the same as a diameter of the inflow end 101 of the valve support 104.

The valve support 104 includes a skirt 112 coupled to a surface thereof. More particularly, the skirt 112 is coupled to an inner surface of the valve support 104 to line a portion thereof. Alternatively, the skirt 112 may be coupled to an outer surface of the valve support 104 to enclose a portion thereof as would be known to one of ordinary skill in the art of prosthetic valve construction. The skirt 112 may be a natural or biological material such as pericardium or another membranous tissue such as intestinal submucosa. Alternatively, the skirt 112 may be a low-porosity woven fabric, such as polyester, Dacron fabric, or PTFE, which creates a one-way fluid passage when attached to the stent. In one embodiment, the skirt 112 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

In an aspect of the disclosure, the anchor element 106 is a stent-like or frame structure that functions as an anchor for the transcatheter heart valve prosthesis 100 to secure its deployed position within a native annulus. The anchor element 106 is a substantially cylindrically-shaped structure that is configured to engage heart tissue at or below an annulus of a native heart valve, such as an annulus of a native mitral valve. At the inflow end 101 of the valve support 104, the anchor element 106 is radially spaced a distance S from the valve support 104 to mechanically isolate the inflow end 101 of the valve support 104 from the anchor element 106. The anchor element 106 includes one or more cleats or prongs 114 that extend outward from an exterior side thereof to engage heart tissue. In another embodiment, the anchor element 106 may employ barbs, spikes, or other tissue fixation mechanisms for engaging heart tissue.

The transcatheter heart valve prosthesis 100 further includes a brim or rim element 116 that extends outwardly from an upstream end of the anchor element 106. The brim element 116 includes overlapping, 180 degree out of phase sinusoidal wire forms that are attached and hinged to the anchor element 106 by a suitable biocompatible low-profile fabric 117 used in bioprosthetic implants namely endovascular grafts, heart valves or left atrial appendage devices to promote bio-integration, such as woven polyethylene terephthalate (PET) fabric. The brim element 116 may act as an atrial retainer, if present, and to serve such a function the brim element 116 may be configured to engage tissue above a native annulus, such as a supra-annular surface or some other tissue in the left atrium, to thereby inhibit downstream migration of a prosthetic heart valve 100, for e.g., during atrial systole.

Figure 2:
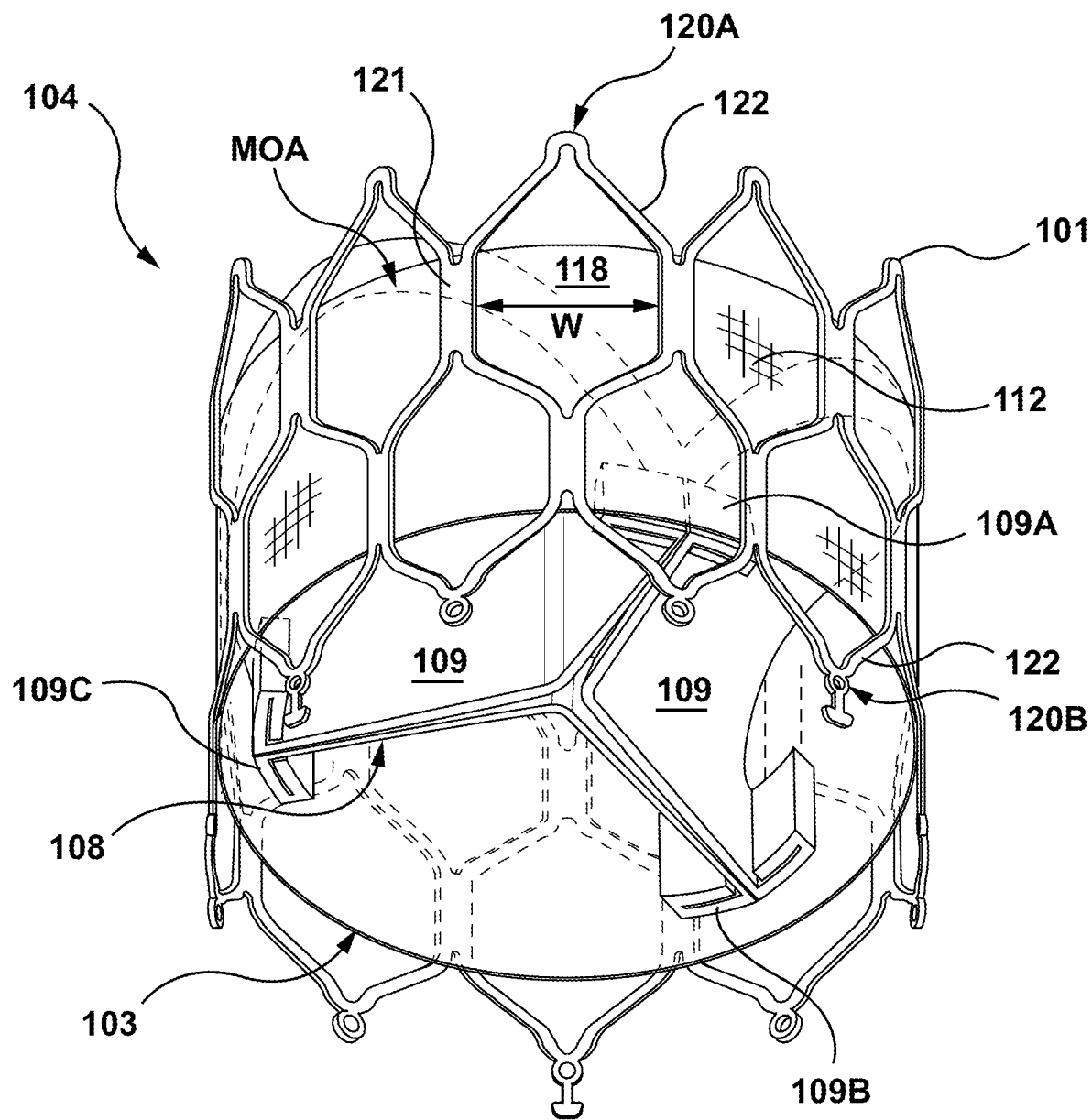
FIG. 2 depicts a perspective view of a valve support of the transcatheter heart valve prosthesis of FIG. 1 with a prosthetic valve component secured therein in accordance with an aspect of the disclosure.
Figure 4:
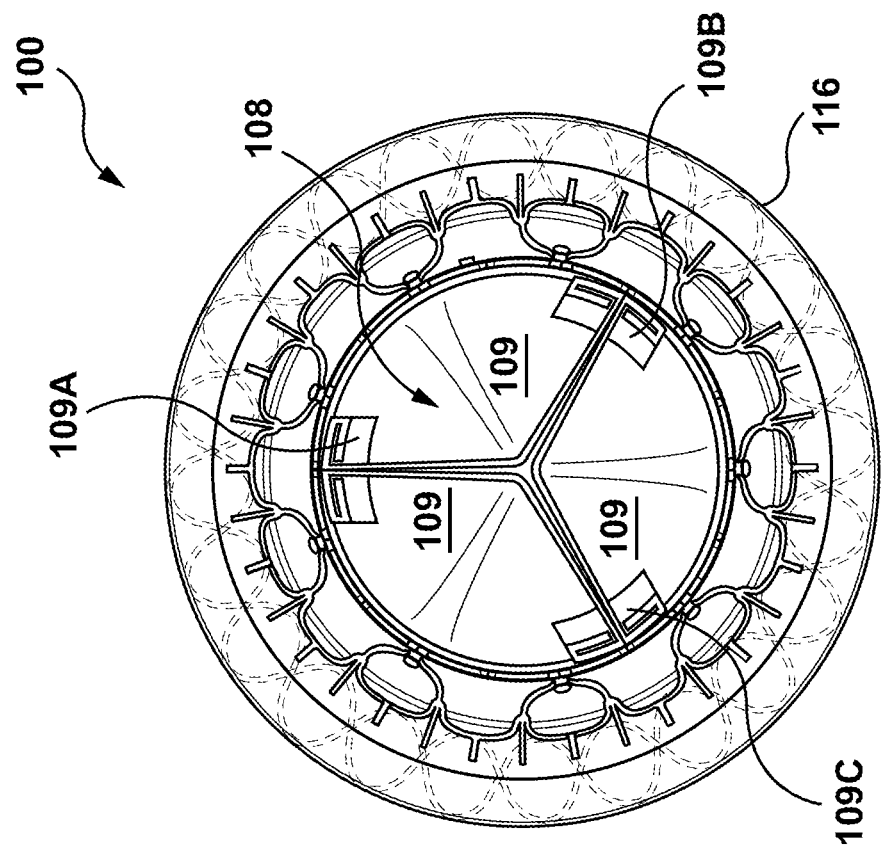
FIG. 4 depicts a ventricular end view of the transcatheter heart valve prosthesis shown in FIG. 1 in accordance with an aspect of the disclosure.
Figure 3:
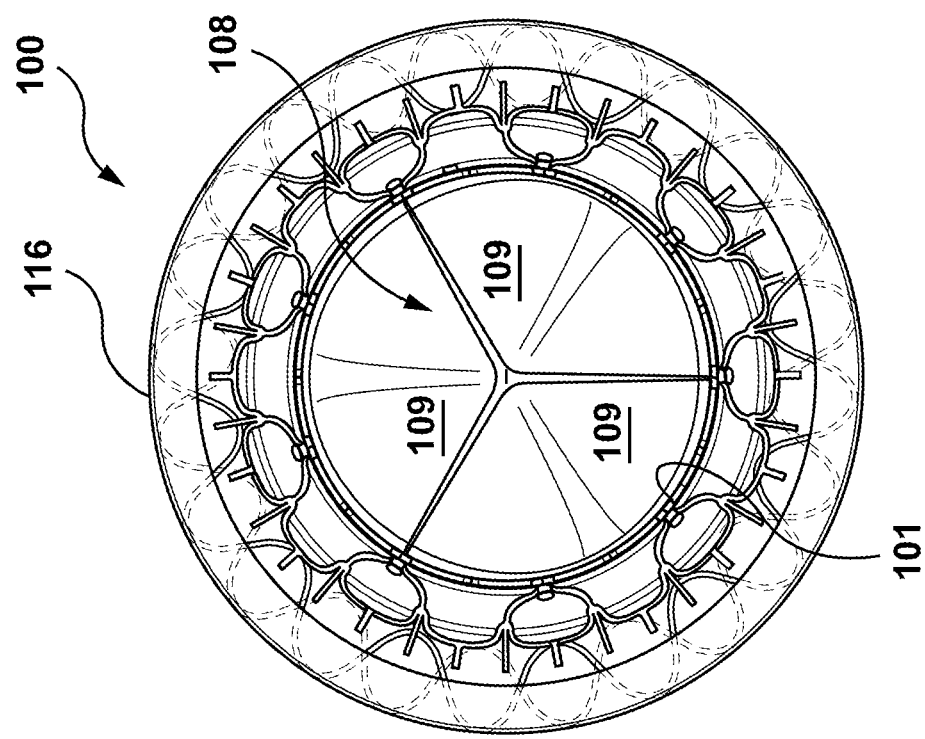
FIG. 3 depicts an atrial end view of the transcatheter heart valve prosthesis shown in FIG. 1 in accordance with an aspect of the disclosure.

The prosthetic valve component 108 of the transcatheter heart valve prosthesis 100 is capable of regulating flow therethrough via valve leaflets that may form a replacement valve. FIGS. 1-6 illustrate an exemplary prosthetic valve component having three leaflets, although a single leaflet or bicuspid leaflet configuration may alternatively be used in embodiments hereof. When deployed in situ, the prosthetic valve component 108 in a closed state is configured to block blood flow in one direction to regulate blood flow through the central lumen 110 of the valve support 104. FIG. 2 depicts a perspective view of the valve support 104 with a prosthetic valve component 108 secured therein, the valve support 104 being shown in FIG. 2 removed from the remainder of the transcatheter heart valve prosthesis 100 shown in FIG. 1 for ease of illustration. FIG. 3 depicts an atrial or inflow end view of the transcatheter heart valve prosthesis 100 shown in FIG. 1, and FIG. 4 depicts a ventricular or outflow end view of the transcatheter heart valve prosthesis 100 shown in FIG. 1. The prosthetic valve component 108 includes valve leaflets 109, e.g., three valve leaflets 109, that are disposed to coapt within an upstream portion of the valve support 104 with leaflet commissures 109A, 109B, 109C of the valve leaflets 109 being secured within a downstream portion of the valve support 104, such that the valve leaflets 109 open during diastole. Leaflets 109 are attached along their bases to the valve support 104, for example, using sutures or a suitable biocompatible adhesive. A margin of attachment, or MOA, is formed at the junction of the leaflets 109 to the valve support 104. Adjoining pairs of leaflets 109 are attached to one another at their lateral ends to form leaflet commissures 109A, 109B, 109C. The orientation of the leaflets 109 within the valve support 104 depends upon on which end of the transcatheter heart valve prosthesis 100 is the inflow end and which end of the transcatheter heart valve prosthesis 100 is the outflow end, thereby ensuring one-way flow of blood through the transcatheter heart valve prosthesis 100.

The valve leaflets 109 may be attached to the skirt 112. The valve leaflets 109 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

For delivery, the transcatheter heart valve prosthesis 100 is radially compressed into a reduced-diameter crimped configuration onto a delivery system for delivery within a vasculature. As known in the art, the delivery system includes an inner shaft that receives the transcatheter heart valve prosthesis 100 on a distal portion thereof and an outer sheath or capsule that is configured to compressively retain the transcatheter heart valve prosthesis 100 on the distal portion of the inner shaft during delivery. Stated another way, the outer sheath or capsule surrounds and constrains the transcatheter heart valve prosthesis 100 in the radially compressed or crimped configuration. An exemplary delivery system for delivering the transcatheter heart valve prosthesis 100 is described in U.S. Pat. No. 9,034,032 to McLean et al. and International Patent Application No. PCT/US2014/029549 to McLean et al, previously incorporated by reference herein. However, it will be apparent to one of ordinary skill in the art that other delivery systems may be utilized and that the components of the delivery system may vary depending upon the configuration and structure of the transcatheter valve prosthesis that is being delivered.

Figure 5:
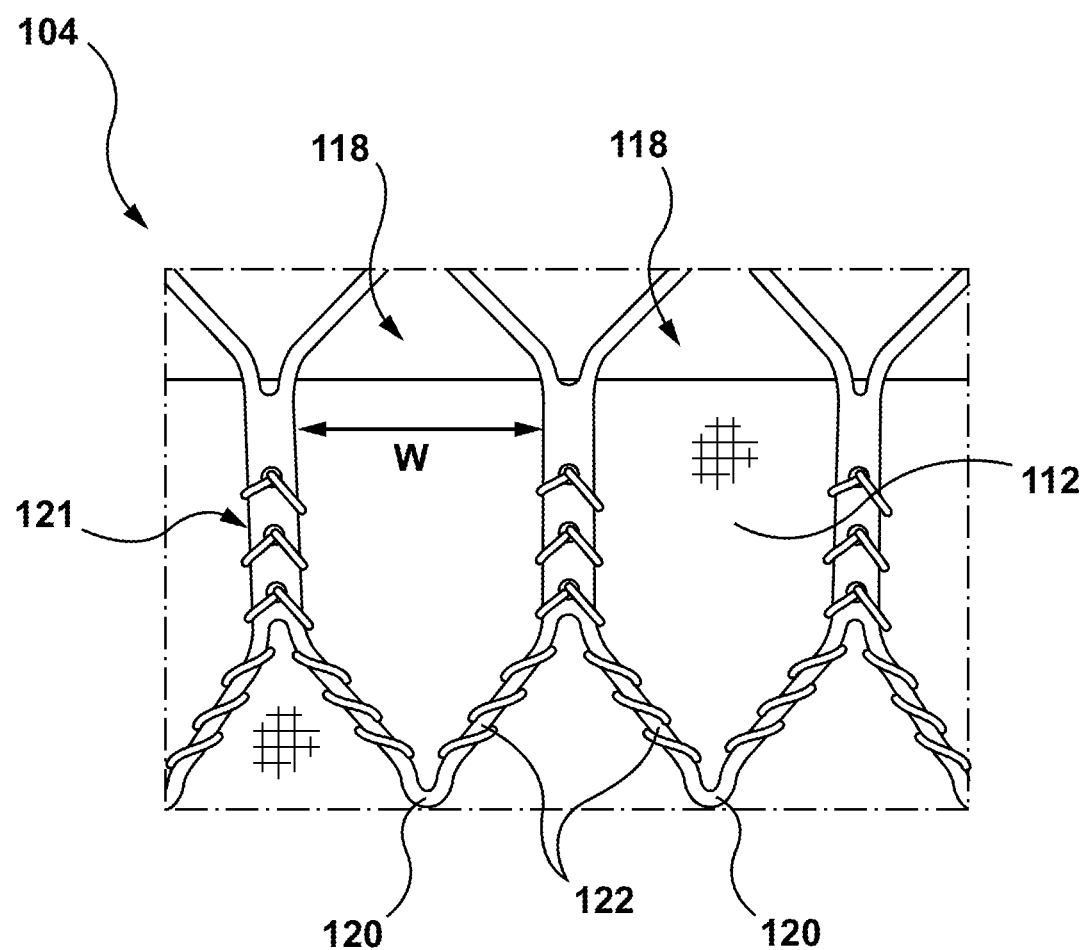
FIG. 5 is an enlarged side view of a side opening of the valve support of FIG. 2.

Referring to FIG. 2 as well as FIG. 5, the structure of the valve support 104 will now be described in more detail. FIG. 5 is an enlarged side view of a plurality of side openings 118 of the valve support 104. The valve support 104 includes a plurality of crowns 120 and a plurality of struts 122 with each crown 120 being formed between a pair of opposing struts 122. Each crown 120 is a curved segment or bend extending between opposing struts 122. The valve support 104 is tubular, with the plurality of side openings 118 being defined by edges of the plurality of crowns 120 and the plurality of struts 122. In an embodiment, the plurality of side openings 118 may be substantially diamond-shaped. The valve support 104 includes a plurality of nodes 121. A node 121 is defined as a region where two crowns of the plurality of crowns 120 within the valve support 104 meet or connect. As best shown in FIG. 5, in this embodiment, the skirt 112 is attached to an inner surface of the valve support 104 around a circumference thereof. The skirt 112 lines the inner surface of the valve support 104 and spans across or extends over each side opening 118 of the plurality of side openings 118. Notably, as shown in FIG. 5, it is not required that the skirt 112 extend over the full opening of each side opening 118. Rather, the skirt 112 may span or cover only a portion of the side opening 118 as shown in FIG. 5.

A series of endmost inflow crowns 120A are formed at the inflow end 101 of the valve support 104, and a series of endmost outflow crowns 120B are formed at the outflow end 103 of the valve support 104. In an embodiment, the inflow end 101 of the valve support 104 has a total of nine endmost inflow crowns 120A around a circumference thereof. The inflow end 101 of the valve support 104 includes a row of side openings 118 around a circumference thereof, and the row has a total of nine side openings 118. Further, outflow end 103 of the valve support 104 has a total of nine endmost inflow crowns 120B around a circumference thereof. The outflow end 103 of the valve support 104 includes a row of side openings 118 around a circumference thereof, and the row has a total of nine side openings 118. In another embodiment hereof (not shown), each of the inflow end 101 and the outflow end 103 of the valve support 104 has between six and nine endmost inflow crowns 120A, 120B around a circumference thereof and includes the row of side openings 118 around a circumference thereof that includes between six and nine side openings 118.

A width W of the side openings 118 is relatively wider as compared to other stents or frames known in the art, thereby resulting a relatively lower total of side openings 118 around a circumference of the valve support 104. In an embodiment, width W is between $1/24^{th}$ and $1/6^{th}$ of the circumference of the valve support 104, or stated another way, between 4% and 16% of the circumference of the valve support 104. By increasing the width of the side openings 118, a lesser amount of material is required for the valve support 104 such that a lower profile may be achieved when the valve support 104 is crimped into a radially compressed configuration for delivery. More particularly, since the frame 102 includes both the valve support 104 and the anchor element 106, it is a challenge to reduce the profile of the transcatheter valve prosthesis 100 in the crimped or radially compressed configuration. The challenge with reducing the profile is that, in the crimped or radially compressed configuration, the incompressible material of the frame 102 imparts high compressive forces on the soft tissue material of the leaflets 109. Such high compressive forces may alter the integrity of the leaflets 109, thereby impacting the long-term durability of the transcatheter valve prosthesis 100. However, increasing the width W of the side openings 118 provides a reduction of the incompressible material of the frame 102, thereby enabling a lower profile in the crimped or radially compressed configuration.

Figure 6A:
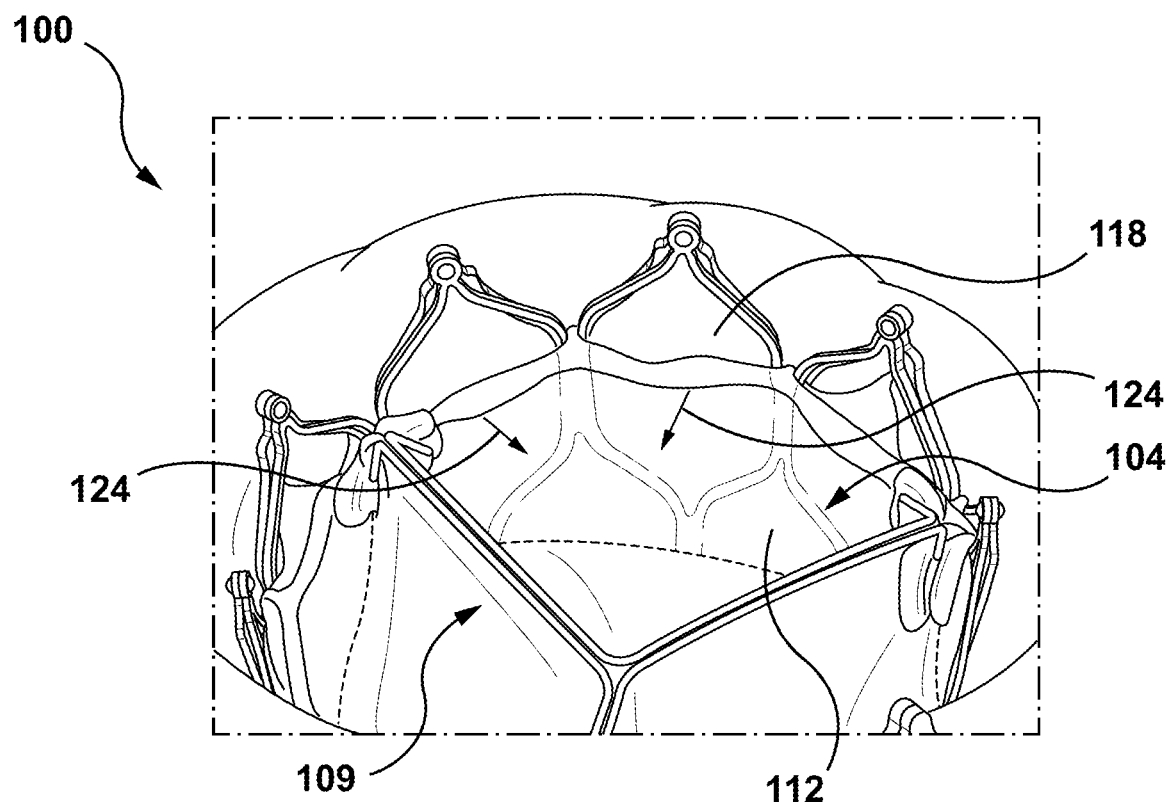
FIG. 6A is a perspective atrial end view of the transcatheter heart valve prosthesis shown in FIG. 1 in accordance with an aspect of the disclosure.
Figure 6B:
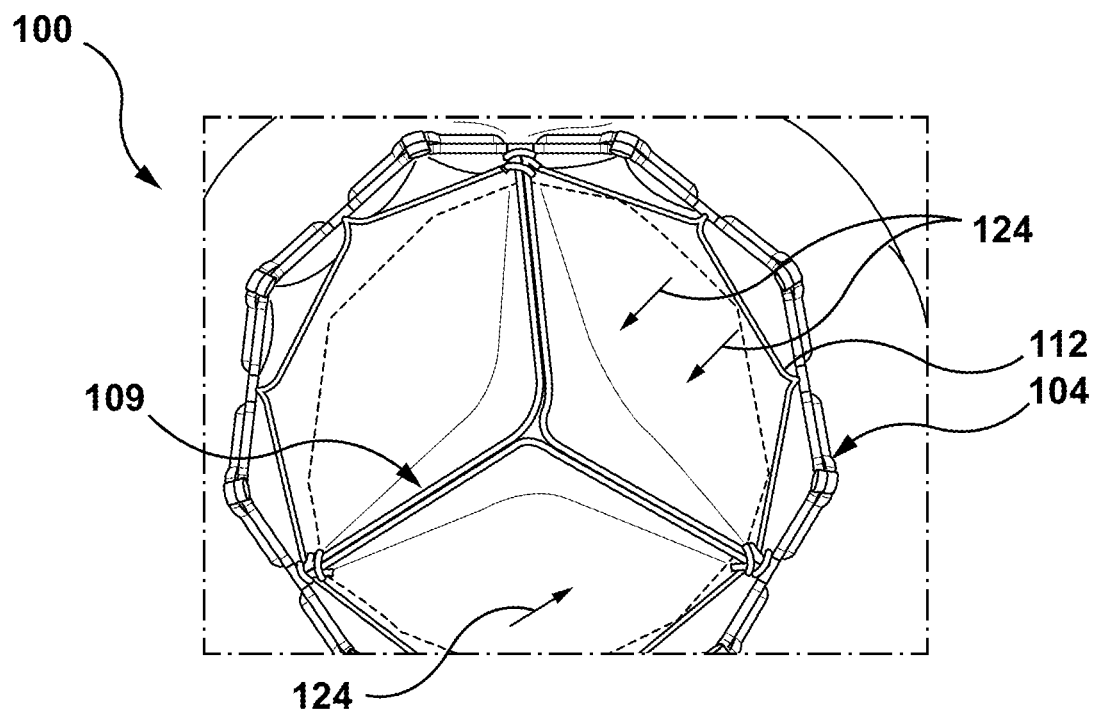
FIG. 6B is an atrial end view of the transcatheter heart valve prosthesis shown in FIG. 1 in accordance with an aspect of the disclosure.

However, reducing the incompressible material of the frame 102 means that the skirt 112 spans a longer distance between nodes 121 or between struts 122. Stated another way, with the width of the side openings 118 being relatively increased as described above, the amount of material of the skirt 112 that spans across the side openings 118 likewise increases and thus a greater amount of material of the skirt 112 is unattached to the valve support 104. Referring now to FIGS. 6A and 6B, when an increased amount of material of the skirt 112 spans across the side openings 118, there is an increased chance of the skirt 112 billowing or moving radially inwards towards the leaflets 109 as indicated by directional arrows 124. The skirt 112 may billow during valve opening and closing in situ, and the leaflets 109 may contact the skirt 112. Such billowing may undesirably result in contact between the skirt 112 and the leaflets 109 of the transcatheter heart valve prosthesis 100. If the leaflets 109 of the transcatheter heart valve prosthesis 100 contact the skirt 112 during opening and closing, such contact may cause early leaflet tissue abrasion as well as early skirt abrasion. Additionally, the greater relative motion between the skirt 112 and the valve support 104 may further induce early skirt abrasion.

Embodiments hereof relate to skirt-reinforcement members that reinforce the material of the skirt 112 that spans across the side openings 118 of the valve support 104 to limit the radial motion or billowing of the skirt material, thereby minimizing risk of damage to both the skirt 112 and the leaflets 109. For sake of illustration, the skirt-reinforcement members described herein are incorporated onto the valve support 104, as the structure of the valve support 104 has already been described in detail above. However, as previously stated, the skirt-reinforcements members described herein may be incorporated onto any stent or frame having a skirt for which reinforcement thereof is desirable to limit billowing, and it is not required that the stent or frame include a prosthetic valve component disposed therein.

Figure 7A:
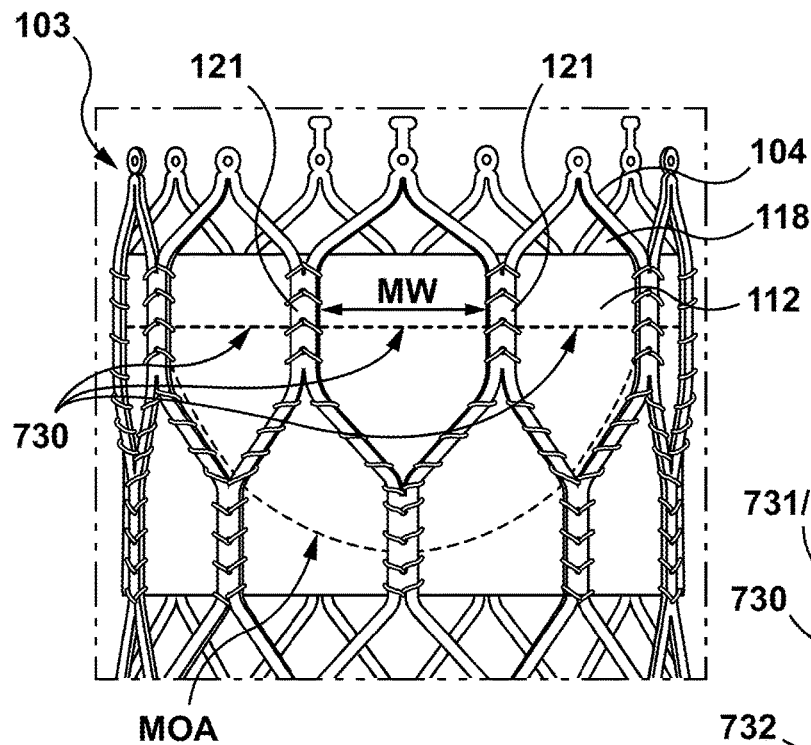
FIG. 7A is a side view of the valve support of the transcatheter heart valve prosthesis of FIG. 1, wherein the valve support further includes a plurality of skirt-reinforcement members in accordance with an aspect of the disclosure.
Figure 7C:
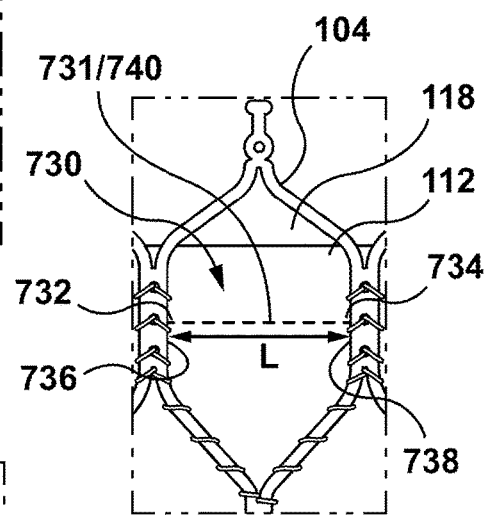
FIG. 7C is an enlarged view of a side opening of the valve support of FIG. 7A.
Figure 7B:
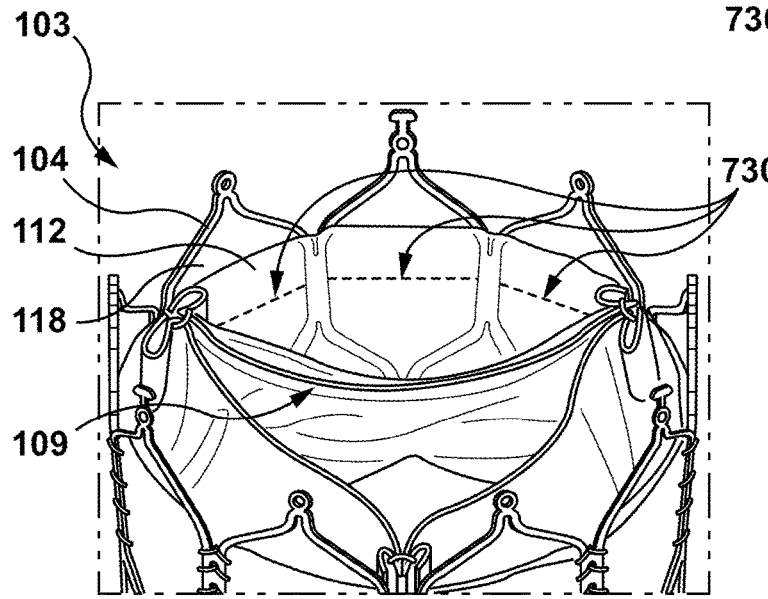
FIG. 7B is a perspective atrial end view of the valve support of FIG. 7A.

Turning to FIGS. 7A and 7B, a skirt-reinforcement member 1330 according to an aspect of the disclosure is illustrated. More particularly, FIG. 7A and FIG. 7B are side and perspective atrial end views, respectively, of the valve support 104 including a plurality of skirt-reinforcement members 730. In the embodiment of FIGS. 7A and 7B, the valve support 104 includes a row of side openings 118 around a circumference thereof and a skirt-reinforcement member 730 spans across or extends over each side opening 118 of the row of side openings 118 around the circumference of the valve support 104. However, it is not required that a skirt-reinforcement member 730 be utilized on every side opening 118 of the row of side openings 118 around the circumference of the valve support 104. Rather, a skirt-reinforcement member 730 may be utilized only on the side openings 118 having skirt material that may come into contact with leaflets 109 when the leaflets are opening and closing in situ. At least one side opening 118 must include a skirt-reinforcement member 730 according to an aspect of the present disclosure. Each skirt-reinforcement member 730 spans a side opening 118 from a first crown or strut edge defining the at least one side opening 118 to a second crown or strut edge defining the at least one side opening 118.

In the embodiment of FIGS. 7A and 7B, each skirt-reinforcement member 730 is a filament or strand 731 of suture that forms a plurality of stitches 740. Exemplary suture materials include but are not limited to a monofilament or plastic suture material, such as polypropylene. Each skirt-reinforcement member 730 is configured to restrict or prevent billowing, or radial motion, of the skirt 112 that spans across or extends over the respective side opening 118. More particularly, each skirt-reinforcement member 730 has a first end 732, a second end 734, and a length L therebetween. The skirt-reinforcement member 730, which includes the plurality of stitches 740, is directly attached to the skirt 112 along its length L. Stated another way, the skirt-reinforcement member 730 is directly attached to the skirt 112 along an unsupported portion of the skirt 112 that spans the respective side opening 118. As used herein, "unsupported portion of the skirt" refers to areas of the skirt 112 in which a surface of the skirt does not directly contact or abut against the valve support 104. The plurality of stitches 740 of the skirt-reinforcement member 730 extends or weaves through the material of the skirt 112 to ensure that the skirt-reinforcement member 730 applies tension to the skirt 112 and thereby prevents undesired billowing of the skirt material.

The first end 732 of the skirt-reinforcement member 730 is attached to a first edge 736 defining the respective side opening 118 and the second end 734 of the skirt-reinforcement member 730 is attached to a second or opposing edge 738 defining the respective side opening 118. Attaching the first and second ends 732, 734 of the skirt-reinforcement member 730 to the valve support 104 ensures that the skirt-reinforcement member 730 has sufficient rigidity to apply tension to the skirt 112 and prevent billowing. More particularly, the first and second ends 732, 734 of the skirt-reinforcement member 730 are attached to the valve support 104 such that the skirt-reinforcement member 730 has sufficient tension along its length L to minimize radial movement of the skirt 112 throughout the cardiac cycle.

As will be described in more detail herein, the first and second ends 732, 734 of the skirt-reinforcement member 730 may be attached to a crown 120 or a strut 122 of the valve support 104. Stated another way, the first and second edges 736, 738 defining the respective side opening 118 may be edges of a crown 120 or a strut 122 of the valve support. In the embodiment depicted in FIGS. 7A and 7B, the first end 732 of the skirt-reinforcement member 730 is circumferentially aligned with the second end 734 of the skirt-reinforcement member 730 such that the skirt-reinforcement member 732 extends substantially perpendicular relative to an axis LA of the valve support 104. The skirt-reinforcement member 730 extends over the side opening 118 in a center or middle thereof, such that the skirt-reinforcement member 730 spans across or extends over the side opening 118 at a maximum width MW thereof. The skirt-reinforcement member 730 spans across the side opening 118 from one node 121 to another node 121 of the valve support 104.

In the embodiment depicted in FIGS. 7A and 7B, adjacent skirt-reinforcement members 730 are circumferentially aligned such that the skirt-reinforcement members 730 collectively circumscribe the valve support 104. However, adjacent skirt-reinforcement members 730 are not required to be circumferentially aligned and further each side opening 118 is not required to include a skirt reinforcement member as described above.

Figure 8A:
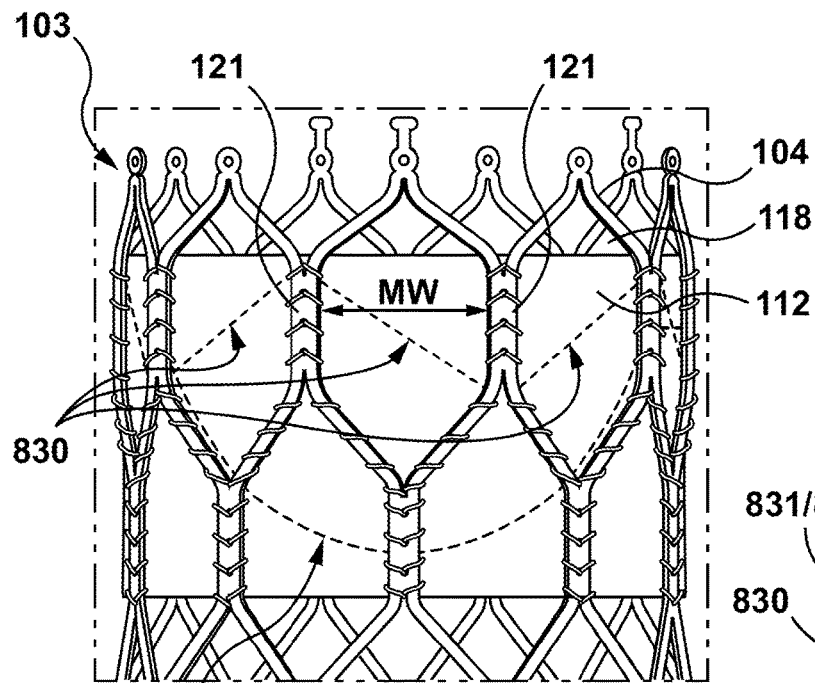
FIG. 8A is a side view of the valve support of the transcatheter heart valve prosthesis of FIG. 1, wherein the valve support further includes a plurality of skirt-reinforcement members in accordance with another aspect of the disclosure.
Figure 8C:
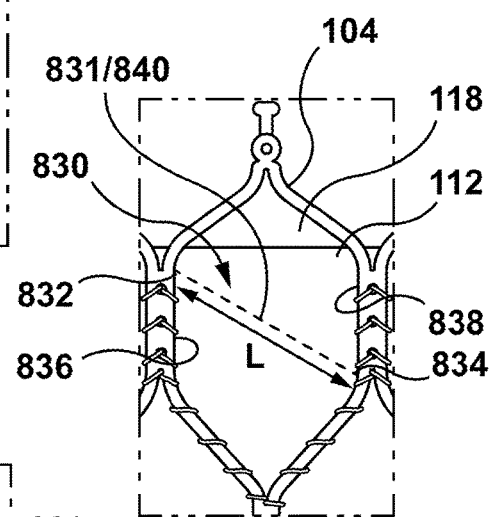
FIG. 8C is an enlarged view of a side opening of the valve support of FIG. 8A.
Figure 8B:
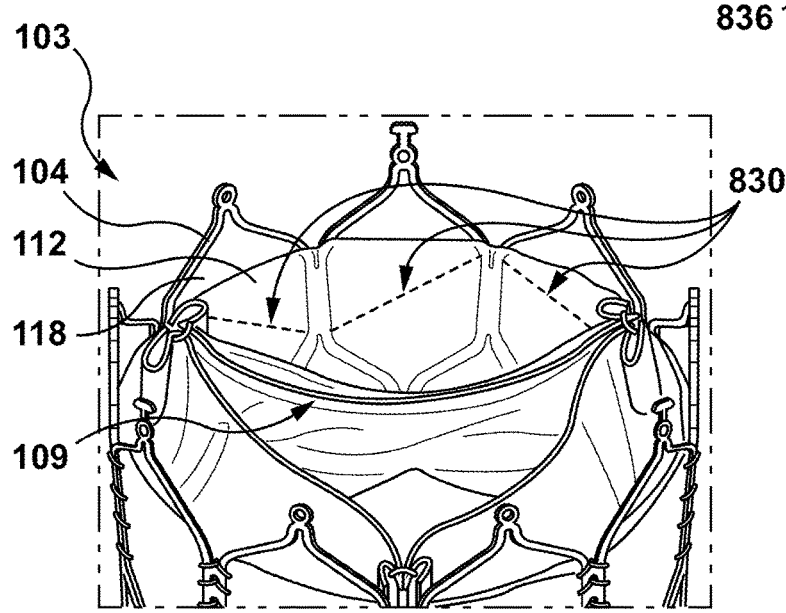
FIG. 8B is a perspective atrial end view of the valve support of FIG. 8A.

Other placements of the skirt-reinforcement members are contemplated herein. For example, in the embodiment depicted in FIGS. 8A and 8B, a first end 832 of a skirt-reinforcement member 830 is circumferentially offset from a second end 834 of the skirt-reinforcement member 830 such that the skirt-reinforcement member 830 is angled relative to the axis LA of the valve support 104. The first end 832 of the skirt-reinforcement member 830 is attached to a first edge 836 defining the respective side opening 118 and the second end 834 of the skirt-reinforcement member 830 is attached to a second or opposing edge 838 defining the respective side opening 118. The skirt-reinforcement member 830 spans diagonally across the side opening 118 from a top end of one node 121 to a bottom end of another node 121 of the valve support 104, or alternatively may span diagonally across the side opening 118 from a node 121 to a strut 122 of the valve support 104. In the embodiment depicted in FIGS. 8A and 8B, adjacent skirt-reinforcement members 830 have alternating orientations (i.e., diagonally downward and diagonally upward) such that the first end 832 of a skirt-reinforcement member 830 circumferentially aligns with a second end 834 of an adjacent skirt-reinforcement member 830 and the skirt-reinforcement members 830 collectively circumscribe the valve support 104 in a zig-zag configuration. However, adjacent skirt-reinforcement members 830 are not required to have alternating orientations and further each side opening 118 is not required to include a skirt reinforcement member as described above.

Figure 9A:
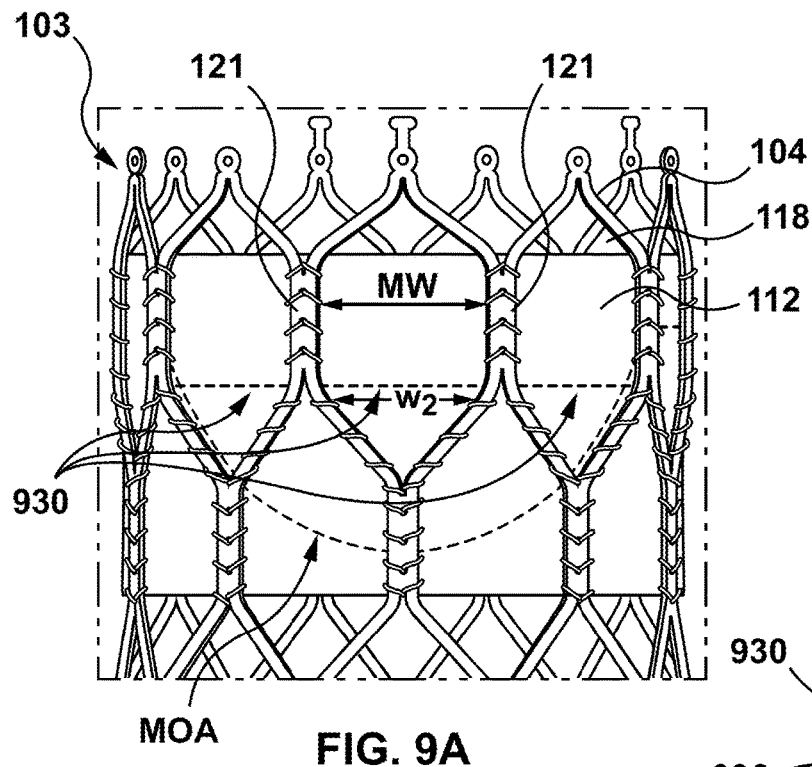
FIG. 9A is a side view of the valve support of the transcatheter heart valve prosthesis of FIG. 1, wherein the valve support further includes a plurality of skirt-reinforcement members in accordance with another aspect of the disclosure.
Figure 9C:
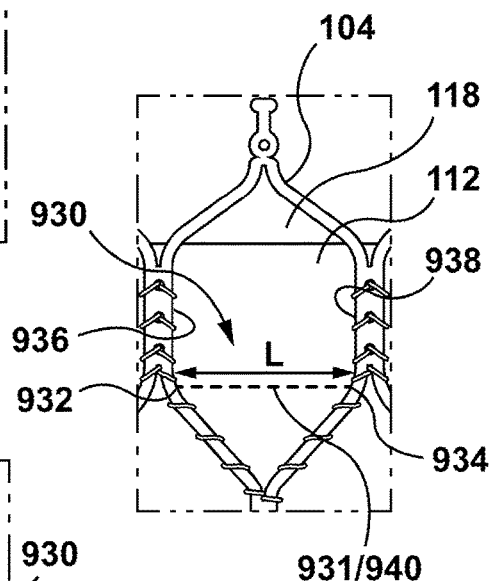
FIG. 9C is an enlarged view of a side opening of the valve support of FIG. 9A.
Figure 9B:
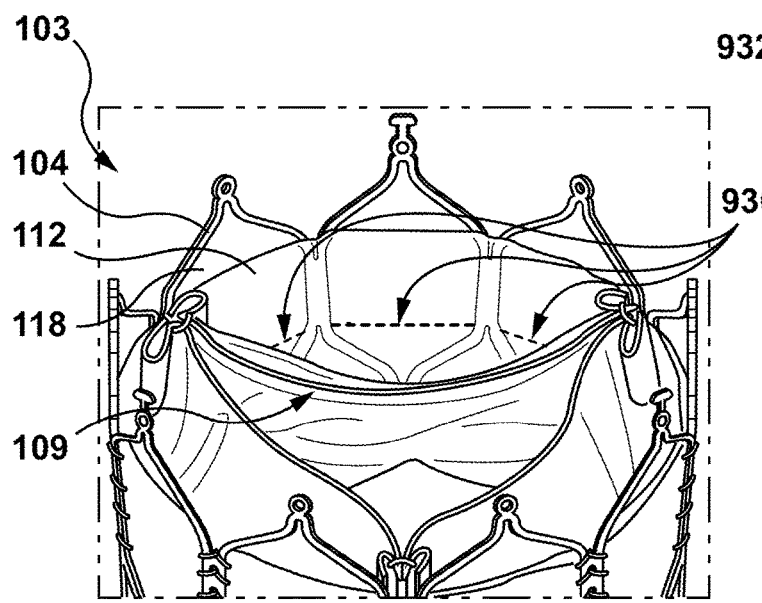
FIG. 9B is a perspective atrial end view of the valve support of FIG. 9A.

In another embodiment depicted in FIGS. 9A and 9B, a first end 932 of a skirt-reinforcement member 930 is aligned with a second end 934 of the skirt-reinforcement member 930 such that the skirt-reinforcement member 932 extends substantially perpendicular relative to the axis LA of the valve support 104 similar to the skirt-reinforcement member 730 described above. The first end 932 of the skirt-reinforcement member 930 is attached to a first edge 936 defining the respective side opening 118 and the second end 934 of the skirt-reinforcement member 930 is attached to a second or opposing edge 938 defining the respective side opening 118. However, in the embodiment of FIGS. 9A and 9B, the skirt-reinforcement member 930 extends over the side opening 118 in a lower region thereof, the lower region having width W2 that is less than the maximum width MW. The skirt-reinforcement member 930 thus spans across or extends over the side opening 118 at the width W2 thereof. The skirt-reinforcement member 930 spans across the side opening 118 from one node 121 to another node 121 of the valve support 104, or alternatively may span across the side opening 118 from one strut 122 to another strut 122 of the valve support 104. In the embodiment depicted in FIGS. 9A and 9B, adjacent skirt-reinforcement members 930 are circumferentially aligned such that the skirt-reinforcement members 930 collectively circumscribe the valve support 104. However, adjacent skirt-reinforcement members 930 are not required to be circumferentially aligned and further each side opening 118 is not required to include a skirt reinforcement member as described above.

Although the above embodiments depict the skirt-reinforcement members 730, 830, 930 having a generally linear or straight configuration within a side opening 118, other configurations of the skirt-reinforcement members are contemplated herein. For example, the skirt-reinforcement members 730, 830, 930 may have a wavy, sinusoidal, or zig-zag configuration along its length or may be configured as "T" or "X" within a side opening 118.

Figure 10A:
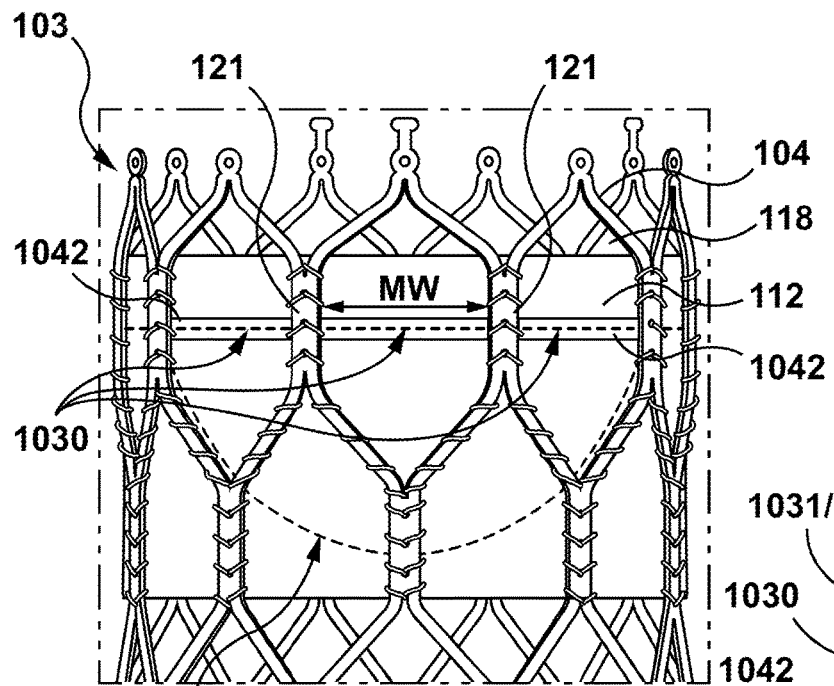
FIG. 10A is a side view of the valve support of the transcatheter heart valve prosthesis of FIG. 1, wherein the valve support further includes a plurality of skirt-reinforcement members in accordance with another aspect of the disclosure.
Figure 10C:
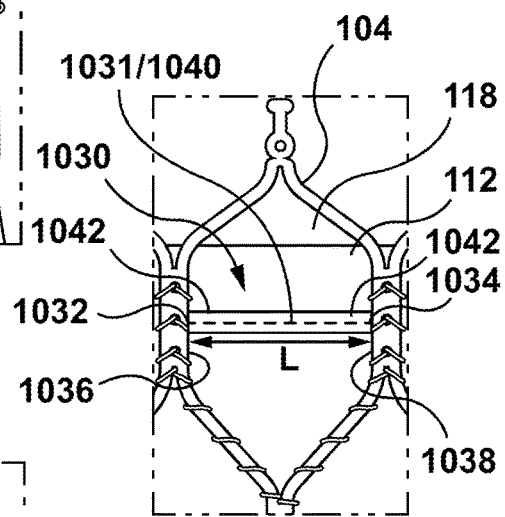
FIG. 10C is an enlarged view of a side opening of the valve support of FIG. 10A.
Figure 10B:
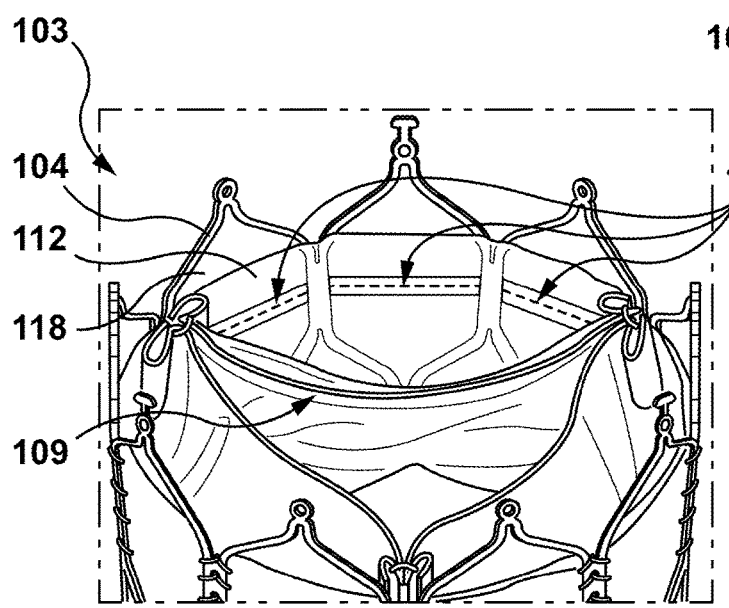
FIG. 10B is a perspective atrial end view of the valve support of FIG. 10A.

Turning to FIGS. 10A and 10B, a skirt-reinforcement member 1030 according to another aspect of the disclosure is illustrated. More particularly, FIG. 10A and FIG. 10B are side and perspective atrial end views, respectively, of the valve support 104 including a plurality of skirt-reinforcement members 1030. In the embodiment of FIGS. 10A and 10B, the valve support 104 includes a row of side openings 118 around a circumference thereof and a skirt-reinforcement member 1030 spans across or extends over each side opening 118 of the row of side openings 118 around the circumference of the valve support 104. However, it is not required that a skirt-reinforcement member 1030 be utilized on every side opening 118 of the row of side openings 118 around the circumference of the valve support 104. Rather, a skirt-reinforcement member 1030 may be utilized only on the side openings 118 having skirt material that may come into contact with leaflets 109 when the leaflets are opening and closing in situ. At least one side opening 118 must include a skirt-reinforcement member 1030 according to an aspect of the present disclosure. Each skirt-reinforcement member 1030 spans a side opening 118 from a first crown or strut edge defining the at least one side opening 118 to a second crown or strut edge defining the at least one side opening 118.

Each skirt-reinforcement member 1030 is similar to the skirt-reinforcement member 730 except that each skirt-reinforcement member 1030 further includes a strip 1042 of fabric or tissue in addition to a filament or strand 1031 of suture that forms a plurality of stitches 1040. The strips 1042 are attached to the skirt 112 via the plurality of stitches 1040 and may be disposed on an outer surface or an inner surface of the skirt 112. Thus, as compared to the skirt-reinforcement member 730 described above which includes a plurality of stitches 740 formed by suture alone, the skirt-reinforcement member 1030 further includes strips 1042 of tissue or fabric in addition to the plurality of stitches 1040 formed by suture and thus provides more robust support or reinforcement.

Similar to the skirt-reinforcement member 730, each skirt-reinforcement member 1030 is configured to restrict or prevent billowing, or radial motion, of the skirt 112 that spans across or extends over the respective side opening 118. More particularly, each skirt-reinforcement member 1030 has a first end 1032, a second end 1034, and a length L therebetween. The length L of the skirt-reinforcement member 1030, which includes the plurality of stitches 1040 and one or more strips 1042 of tissue or fabric, is directly attached to the skirt 112 along its length L. Stated another way, the skirt-reinforcement member 1030 is directly attached to the skirt 112 along an unsupported portion of the skirt 112 that spans the respective side opening 118. The plurality of stitches 1040 of the skirt-reinforcement member 1030 extends or weaves through the material of the skirt 112 and through the material of the strips 1042 of tissue or fabric, to ensure that the skirt-reinforcement member 1030 applies tension to the skirt 112 and thereby prevents undesired billowing of the skirt material.

The first end 1032 of the skirt-reinforcement member 1030 is formed by the strand 1031 of suture of the skirt-reinforcement member 1030, and is attached to a first edge 1036 defining the respective side opening 118. The second end 1034 of the skirt-reinforcement member 1030 is also formed by the strand 1031 of suture of the skirt-reinforcement member 1030, and is attached to a second or opposing edge 1038 defining the respective side opening 118. Attaching the first and second ends 1032, 1034 of the skirt-reinforcement member 1030 to the valve support 104 ensures that the skirt-reinforcement member 1030 has sufficient rigidity to apply tension to the skirt 112 and prevent billowing. More particularly, the first and second ends 1032, 1034 of the skirt-reinforcement member 1030 are attached to the valve support 104 such that the skirt-reinforcement member 1030 has sufficient tension along its length L to minimize radial movement of the skirt 112 throughout the cardiac cycle.

The first and second ends 1032, 1034 of the skirt-reinforcement member 1030 may be attached to a crown 120 or a strut 122 of the valve support 104. Stated another way, the first and second edges 1036, 1038 defining the respective side opening 118 may be edges of a crown 120 or a strut 122 of the valve support. In the embodiment depicted in FIGS. 10A and 10B, the first end 1032 of the skirt-reinforcement member 1030 is aligned with the second end 1034 of the skirt-reinforcement member 1030 such that the skirt-reinforcement member 1032 extends substantially perpendicular relative to an axis LA of the valve support 104. The skirt-reinforcement member 1030 extends over the side opening 118 in a center or middle thereof, such that the skirt-reinforcement member 1030 spans across or extends over the side opening 118 at a maximum width MW thereof. The skirt-reinforcement member 1030 spans across the side opening 118 from one node 121 to another node 121 of the valve support 104.

The strips 1042 may be a natural or biological material such as pericardium or another membranous tissue such as intestinal submucosa. Alternatively, the strips 1042 may be a low-porosity woven or knit fabric, such as polyester, Dacron fabric, or PTFE knit. Exemplary suture materials for the strand 1031 include but are not limited to a monofilament or plastic suture material, such as polypropylene.

The strips 1042 are relatively thin and have a thickness between 0.1 mm and 0.5 mm, and have a height (in the axial direction of the valve support 104) between 0.2 mm up to the full height of the side opening 118. The length of each strip 1042 is substantially the same as the length L of the strip-reinforcement member 1030 such that the strip 1042 extends substantially between the first end 1032 and the second end 1034 of the strip-reinforcement member 1030.

In another embodiment, the strip 1042 of fabric or tissue may be attached to the skirt 112 with a different fixation mechanism as an alternative to the plurality of stitches 1040. For example, in another embodiment, the strip 1042 of fabric or tissue may be attached to the skirt 112 using adhesive. When utilizing adhesive as a fixation mechanism, the strip 1042 of fabric or tissue is disposed onto the skirt in a taut configuration to ensure that the skirt-reinforcement member 1030 applies tension to the skirt 112 and thereby prevents undesired billowing of the skirt material. Further, the adhesive may retract as it cures to apply further tension to the skirt material. Adhesive as a fixation mechanism provides more predictable packing or folding of the valve support 104 when the valve support 104 is collapsed into the radially compressed or crimped configuration for delivery.

In the embodiment depicted in FIGS. 10A and 10B, adjacent skirt-reinforcement members 1030 are circumferentially aligned such that the skirt-reinforcement members 1030 collectively circumscribe the valve support 104. However, adjacent skirt-reinforcement members 1030 are not required to be circumferentially aligned and further each side opening 118 is not required to include a skirt reinforcement member as described above.

Figure 11A:
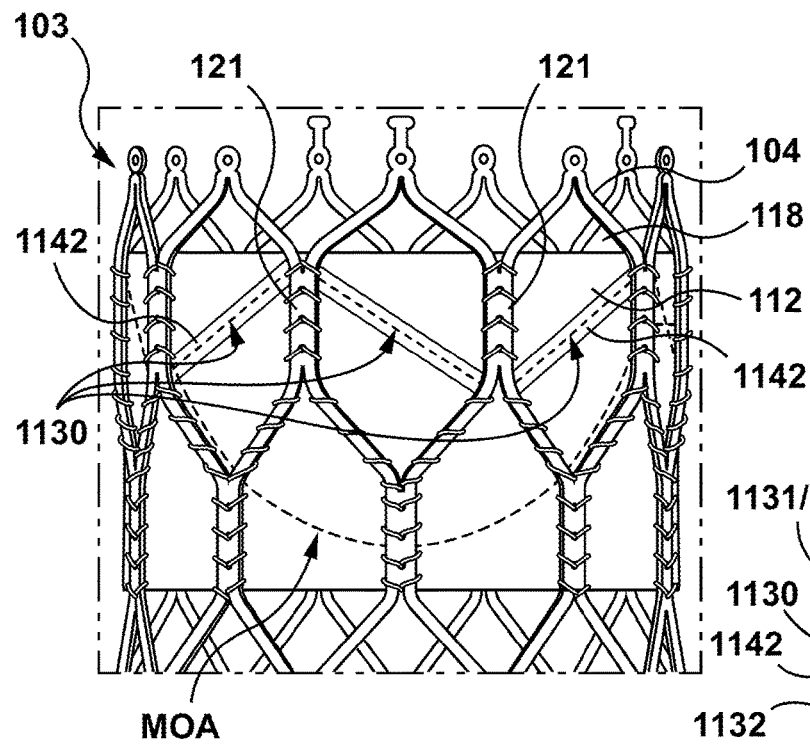
FIG. 11A is a side view of the valve support of the transcatheter heart valve prosthesis of FIG. 1, wherein the valve support further includes a plurality of skirt-reinforcement members in accordance with another aspect of the disclosure.
Figure 11C:
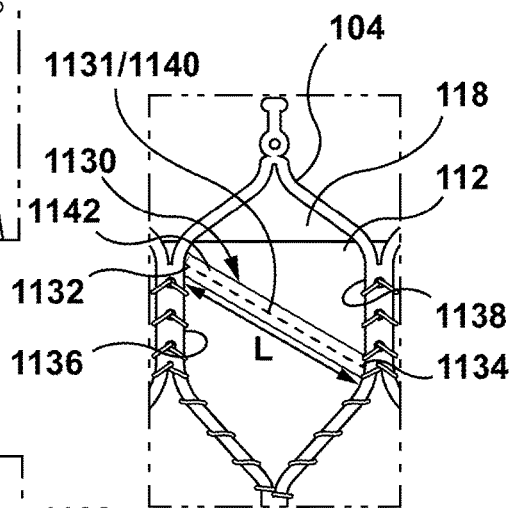
FIG. 11C is an enlarged view of a side opening of the valve support of FIG. 11A.
Figure 11B:
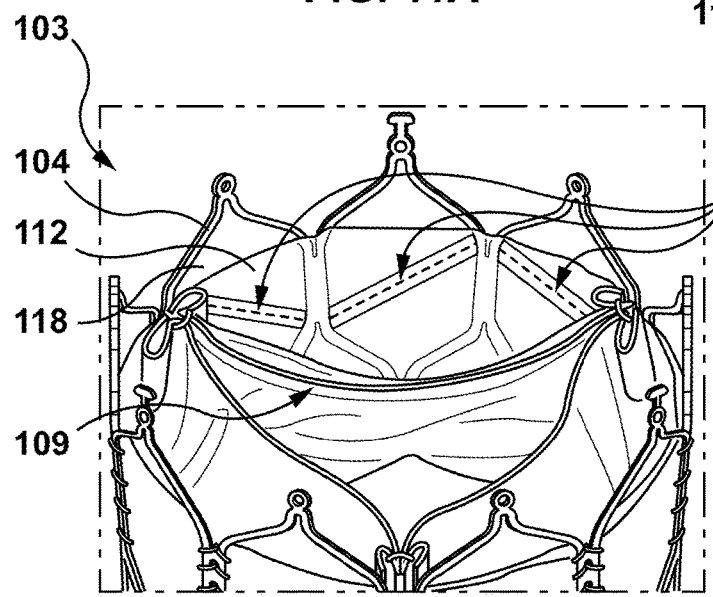
FIG. 11B is a perspective atrial end view of the valve support of FIG. 11A.

Other placements of the skirt-reinforcement member 1030 are contemplated herein. For example, in the embodiment depicted in FIGS. 11A and 11B, a first end 1132 of a skirt-reinforcement member 1130 is offset from a second end 1134 of the skirt-reinforcement member 1130 such that the skirt-reinforcement member 1130 is angled relative to the axis LA of the valve support 104. The first end 1132 of the skirt-reinforcement member 1130 is attached to a first edge 1136 defining the respective side opening 118 and the second end 1134 of the skirt-reinforcement member 1130 is attached to a second or opposing edge 1138 defining the respective side opening 118. The skirt-reinforcement member 1130 spans diagonally across the side opening 118 from a top end of one node 121 to a bottom end of another node 121 of the valve support 104, or alternatively may span diagonally across the side opening 118 from a node 121 to a strut 122 of the valve support 104. In the embodiment depicted in FIGS. 11A and 11B, adjacent skirt-reinforcement members 1130 have alternating orientations (i.e., diagonally downward and diagonally upward) such that the first end 1132 of a skirt-reinforcement member 1130 circumferentially aligns with a second end 1134 of an adjacent skirt-reinforcement member 1130 and the skirt-reinforcement members 1130 collectively circumscribe the valve support 104 in a zig-zag configuration. However, adjacent skirt-reinforcement members 1130 are not required to have alternating orientations and further each side opening 118 is not required to include a skirt reinforcement member as described above.

Figure 12A:
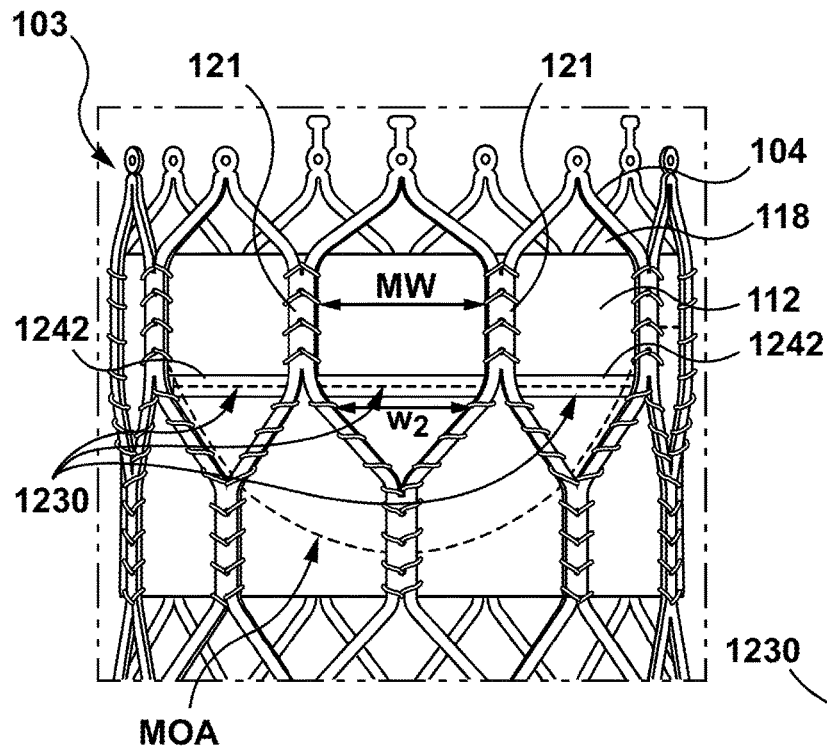
FIG. 12A is a side view of the valve support of the transcatheter heart valve prosthesis of FIG. 1, wherein the valve support further includes a plurality of skirt-reinforcement members in accordance with another aspect of the disclosure.
Figure 12C:
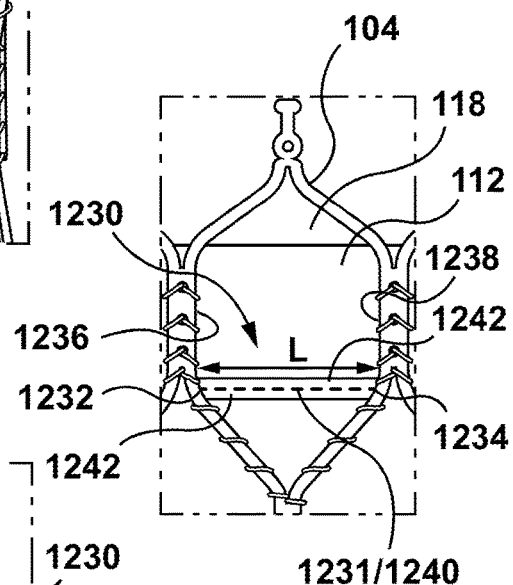
FIG. 12C is an enlarged view of a side opening of the valve support of FIG. 12A.
Figure 12B:
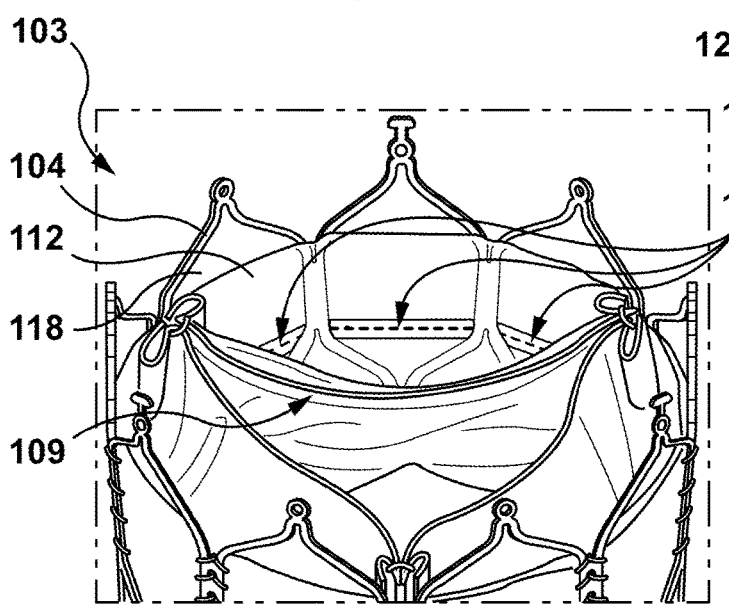
FIG. 12B is a perspective atrial end view of the valve support of FIG. 12A.

In another embodiment depicted in FIGS. 12A and 12B, a first end 1232 of a skirt-reinforcement member 1230 is aligned with a second end 1234 of the skirt-reinforcement member 1230 such that the skirt-reinforcement member 1232 extends substantially perpendicular relative to the axis LA of the valve support 104 similar to the skirt-reinforcement member 1030 described above. The first end 1232 of the skirt-reinforcement member 1230 is attached to a first edge 1236 defining the respective side opening 118 and the second end 1234 of the skirt-reinforcement member 1230 is attached to a second or opposing edge 1238 defining the respective side opening 118. However, in the embodiment of FIGS. 12A and 12B, the skirt-reinforcement member 1230 extends over the side opening 118 in a lower region thereof, the lower region having width W2 that is less than the maximum width MW. The skirt-reinforcement member 1230 thus spans across or extends over the side opening 118 at the width W2 thereof. The skirt-reinforcement member 1230 spans across the side opening 118 from one node 121 to another node 121 of the valve support 104, or alternatively may span across the side opening 118 from one strut 122 to another strut 122 of the valve support 104. In the embodiment depicted in FIGS. 12A and 12B, adjacent skirt-reinforcement members 1230 are circumferentially aligned such that the skirt-reinforcement members 1230 collectively circumscribe the valve support 104. However, adjacent skirt-reinforcement members 1230 are not required to be circumferentially aligned and further each side opening 118 is not required to include a skirt reinforcement member as described above.

Although the above embodiments depict the skirt-reinforcement members 1030, 1130, 1230 having a generally linear or straight configuration, other configurations of the skirt-reinforcement members are contemplated herein. For example, the skirt-reinforcement members 1030, 1130, 1230 may have a wavy, sinusoidal, or zig-zag configuration along its length or may be configured as "T" or "X" within the side opening 118.

Figure 13A:
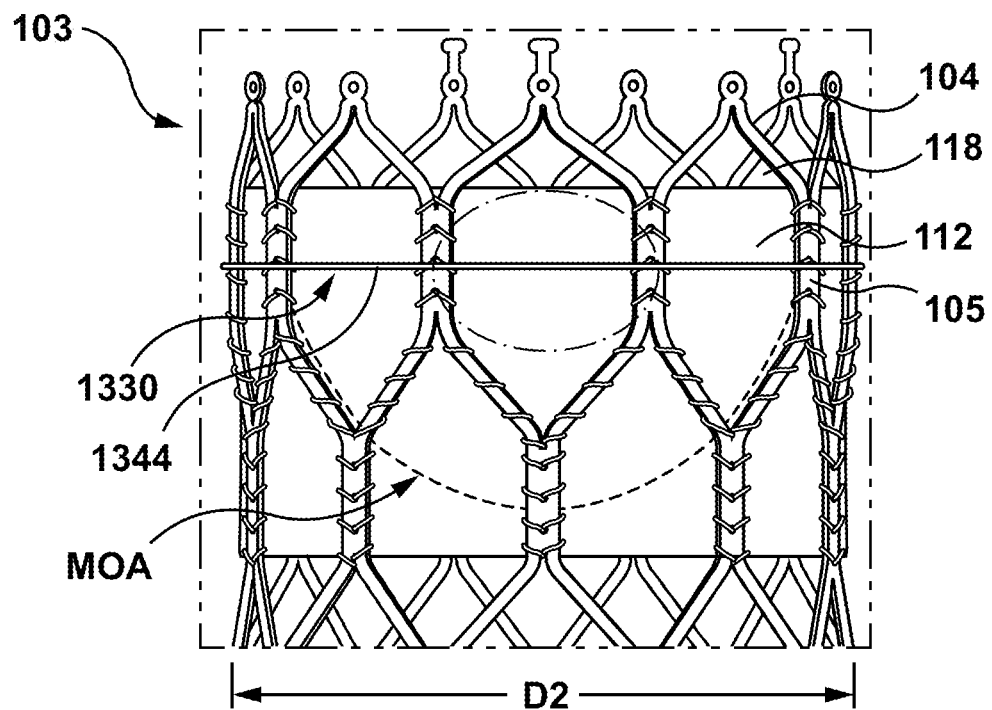
FIG. 13A is a side view of the valve support of the transcatheter heart valve prosthesis of FIG. 1, wherein the valve support includes a skirt-reinforcement member that circumscribes an outer surface of the valve support.
Figure 13B:
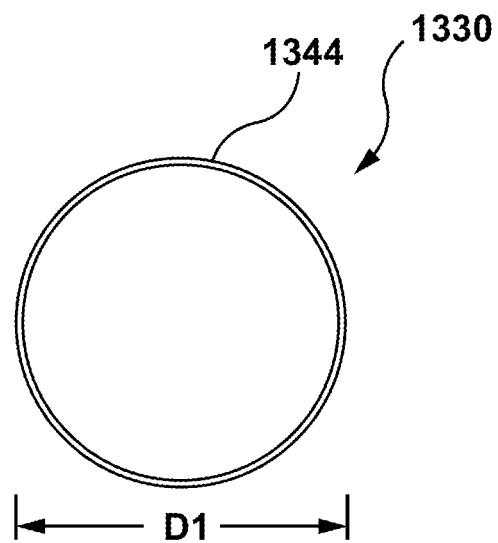
FIG. 13B is a top view of the skirt-reinforcement member of FIG. 13A, wherein the skirt-reinforcement member is removed from the valve support for purposes of illustration only.

Turning now to FIG. 13A and FIG. 13B, a skirt-reinforcement member 1330 according to another aspect of the disclosure is illustrated. More particularly, FIG. 13A is side view of the valve support 104 including the skirt-reinforcement member 1330 and FIG. 13B illustrates a top view of the skirt-reinforcement member 1330 removed from the valve support 104 for sake of illustration. In the embodiment of FIG. 13A and FIG. 13B, the skirt-reinforcement member 1330 is a continuous band or ring 1344 that extends 360° around an outer surface 105 of the valve support 104. Stated another way, the skirt-reinforcement member 1330 is circumferentially disposed around the perimeter of the valve support 104 and encircles or circumscribes the outer surface 105 of the valve support 104. The ring 1344 is an elastic material and a diameter D1 of the skirt-reinforcement member 1330 is approximately the same as a diameter D2 of the valve support 104 when the valve support 104 is in its radially expanded configuration.

Notably, the ring 1344 is directly attached to the skirt 112 along portions thereof that span across or extend over the side openings 118 of the valve support 104 but the ring 1344 is not directly attached to the valve support 104. Stated another way, when the ring 1344 and the valve support 104 meet or intersect, the ring 1344 overlaps or overlays the valve support 104 but is not otherwise attached thereto. The ring 1344 is however attached to the skirt 112 to apply tension to the skirt 112 and thereby restrict or prevent billowing of the skirt 112 that spans across or extends over the side openings 118 of the valve support 104. Thus, when the ring 1344 and the skirt 112 meet or intersect, the ring 1344 overlaps or overlays the skirt 112 and is further directly attached thereto. Since the ring 1344 is directly attached to the skirt 112, is formed from an elastic material, and has the diameter D that is approximately the same as the expanded diameter of the valve support 104, the skirt-reinforcement member 1330 has sufficient tension to minimize radial movement of the skirt 112 throughout the cardiac cycle. As such, the skirt-reinforcement member 1330 is configured to minimize radial movement of the skirt 112 and better protect the leaflets 109 from abrasion as well as prevent skirt degradation.

The ring 1344 may be attached to the skirt 112 via any suitable attachment mechanism, including but not limited to suture, adhesive, or welding. Suitable elastic materials for the ring 1344 include but are not limited to polymer materials such as polyurethane or silicone, as well as biological or natural materials such as pericardium or another membranous tissue such as intestinal submucosa. "Elastic" as used herein includes materials that may be stretched or elongated to fit over and around the outer surface 105 of the valve support 104, while also having sufficient resiliency to resume their original size/configuration and conform to the outer surface 105 of the valve support 104. The elastic material of the ring 1344 has sufficient resiliency to conform to and be secured over the outer surface 105 of the valve support 104, but does not exert an amount of force that would result in constriction or reduction of the inner diameter of the valve support 104.

As stated above, the skirt-reinforcement members 730, 830, 930, 1030, 1130, 1230, 1330 may be utilized on any transcatheter heart valve prosthesis that includes a skirt on a portion thereof. The skirt-reinforcement members 730, 830, 930, 1030, 1130, 1230, 1330 serve to limit the radial motion or billowing of the skirt material, thereby minimizing risk of damage to both the skirt and the leaflets. Depending on the configuration of the frame, the particular placement of the skirt-reinforcement members may vary. In an embodiment, the skirt-reinforcement members are positioned downstream of a margin of attachment (MOA) of the leaflets of the transcatheter heart valve prosthesis and are positioned over a side opening of the frame that includes skirt material over a portion thereof. The configuration of the frame and the configuration of the side opening of the frame is non-limiting and may vary, as exemplified in the following figures.

Figure 14:
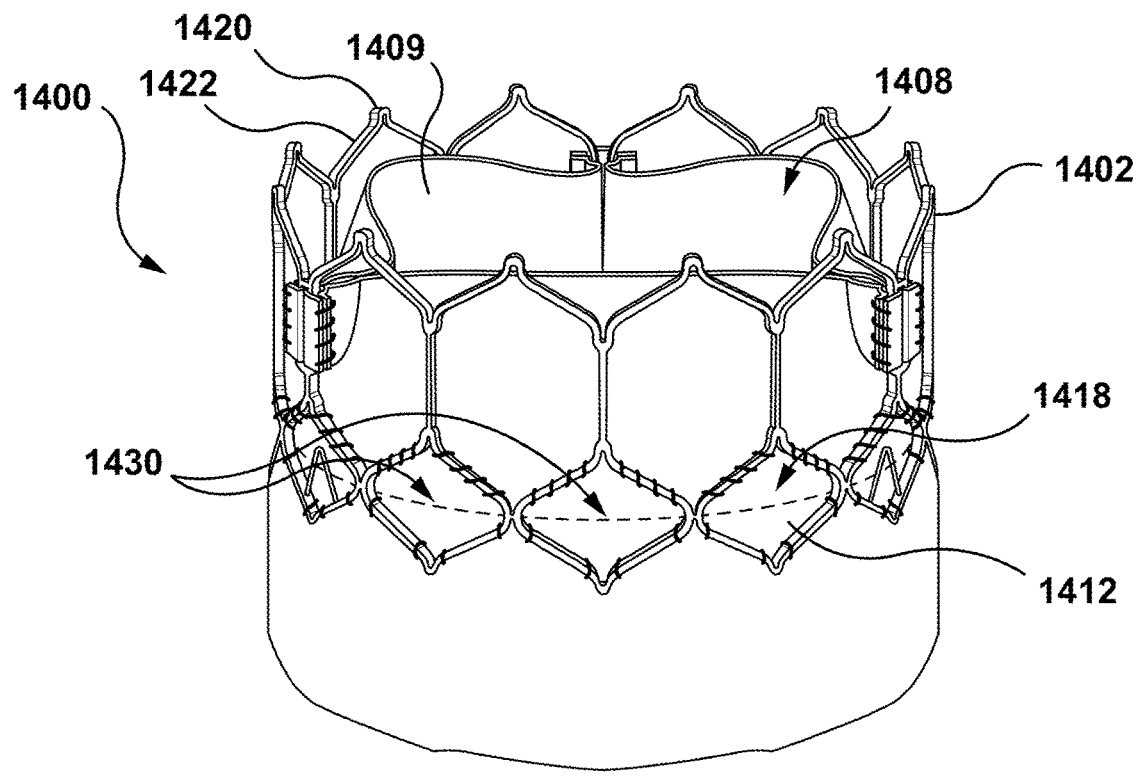
FIG. 14 depicts a perspective view of a transcatheter heart valve prosthesis in accordance with another aspect of the disclosure, wherein the frame further includes a plurality of skirt-reinforcement members.

FIG. 14 depicts a perspective view of a transcatheter heart valve prosthesis 1400 in accordance with another aspect of the disclosure. The transcatheter heart valve prosthesis 1400 includes a stent or frame 1402 and a prosthetic valve component 1408 including at least one leaflet disposed within and secured to the frame 1402. The frame 1402 includes a plurality of crowns 1420 and a plurality of struts 1422 with each crown 1420 being formed between a pair of opposing struts 1422. Each crown 1420 is a curved segment or bend extending between opposing struts 1422. The frame 1402 is tubular, with the plurality of side openings 1418 being defined by edges of the plurality of crowns 1420 and the plurality of struts 1422. In an embodiment, the plurality of side openings 1418 may be substantially diamond-shaped.

The frame 1402 includes a skirt 1412 coupled to a surface thereof. More particularly, the skirt 1412 is coupled to an inner surface of the frame 1402 to line a portion thereof. Alternatively, the skirt 1412 may be coupled to an outer surface of the frame 1402 to enclose a portion thereof as would be known to one of ordinary skill in the art of prosthetic valve construction. The skirt 1412 may be formed from the same materials described above with respect to the skirt 112.

The prosthetic valve component 1408 of the transcatheter heart valve prosthesis 1400 is capable of regulating flow therethrough via valve leaflets that may form a replacement valve. FIG. 14 illustrates an exemplary prosthetic valve component having three leaflets 1409, although a single leaflet or bicuspid leaflet configuration may alternatively be used in embodiments hereof. As described above with respect to the prosthetic valve component 108, when deployed in situ, the prosthetic valve component 1408 in a closed state is configured to block blood flow in one direction to regulate blood flow through a central lumen of the frame 1402.

The valve leaflets 1409 may be attached to the skirt 1412. The skirt 1412 may billow during valve opening and closing in situ, and the leaflets 1409 may contact the skirt 1412. Such billowing may undesirably result in contact between the skirt 1412 and the leaflets 1409 of the transcatheter heart valve prosthesis 1400. If the leaflets 1409 of the transcatheter heart valve prosthesis 1400 contact the skirt 1412 during opening and closing, such contact may cause early leaflet tissue abrasion as well as early skirt abrasion. Additionally, the greater relative motion between the skirt 1412 and the frame 1402 may further induce early skirt abrasion. Thus, the transcatheter heart valve prosthesis 1400 further includes a plurality of skirt-reinforcement members 1430. As described above with respect to the skirt-reinforcement members 730 described above, the skirt-reinforcement members 1430 reinforce the material of the skirt 1412 that spans across the side openings 1418 of the frame 1402 to limit the radial motion or billowing of the skirt material, thereby minimizing risk of damage to both the skirt 1412 and the leaflets 1409.

In the embodiment of FIG. 14, the frame 1402 includes a row of side openings 1418 around a circumference thereof and a skirt-reinforcement member 1430 spans across or extends over each side opening 1418 of the row of side openings 1418 around the circumference of the frame 1402. However, it is not required that a skirt-reinforcement member 1430 be utilized on every side opening 1418 of the row of side openings 1418 around the circumference of the frame 1402. Rather, a skirt-reinforcement member 1430 may be utilized only on the side openings 1418 having skirt material that may come into contact with leaflets 1409 when the leaflets are opening and closing in situ. At least one side opening 1418 must include a skirt-reinforcement member 1430 according to an aspect of the present disclosure. Further, the placement of the skirt-reinforcement members 1430 is exemplary only and the skirt-reinforcement members 1430 may be disposed on side openings 1418 of different rows from that depicted on FIG. 14.

Figure 14A:
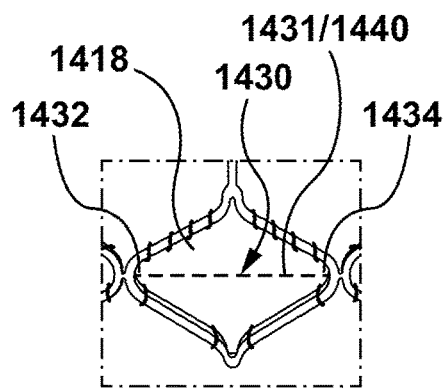
FIG. 14A is an enlarged view of a side opening of the transcatheter heart valve prosthesis of FIG. 14.

FIG. 14A is an enlarged view of a side opening 1418 of the frame 1402 that includes a skirt-reinforcement member 1430. Each skirt-reinforcement member 1430 spans a side opening 1418 from a first crown or strut edge defining the at least one side opening 1418 to a second crown or strut edge defining the at least one side opening 1418. In the embodiments of FIGS. 14-14A, the skirt-reinforcement members 1430 are the same as the skirt-reinforcement members 730. Each skirt-reinforcement member 1430 is a filament or strand 1431 of suture that forms a plurality of stitches 1440. The skirt-reinforcement member 1430 is directly attached to the skirt 1412 along an unsupported portion of the skirt 1412 that spans the respective side opening 1418. The plurality of stitches 1440 of the skirt-reinforcement member 1430 extends or weaves through the material of the skirt 1412 to ensure that the skirt-reinforcement member 1430 applies tension to the skirt 1412 and thereby prevents undesired billowing of the skirt material. The first and second ends 1432, 1434 of the skirt-reinforcement member 1430 are attached to the frame 1402 such that the skirt-reinforcement member 1430 has sufficient tension along its length to minimize radial movement of the skirt 1412 throughout the cardiac cycle.

Figure 14B:
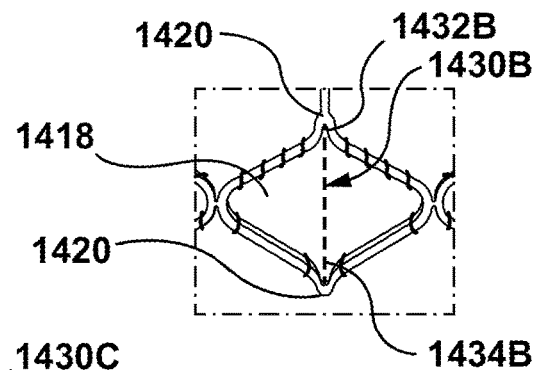
FIG. 14B is an enlarged view of a side opening of a transcatheter heart valve prosthesis according to another embodiment hereof, wherein a skirt-reinforcement member extends in a vertical orientation.

In FIGS. 14 and 14A, the skirt-reinforcement member 1430 extends in a horizontal orientation over the side opening 1418 in a center or middle thereof. However, other placements of the skirt-reinforcement members are contemplated herein. For example, in the embodiment depicted in FIG. 14B, a skirt-reinforcement member 1430B extends in a vertical orientation over the side opening 1418 in a center or middle thereof. A first end 1432B of a skirt-reinforcement member 1430B is longitudinally offset from a second end 1434B of the skirt-reinforcement member 1430B such that the skirt-reinforcement member 1430B is parallel or substantially parallel relative to the axis LA of the frame. The first end 1432B of the skirt-reinforcement member 1430B is attached to a first crown 1420B defining the respective side opening 1418 and the second end 1434B of the skirt-reinforcement member 1430 is attached to a second or opposing crown 1420B defining the respective side opening 1418 such that the skirt-reinforcement member 1430B spans vertically across the side opening 1418.

Figure 14C:
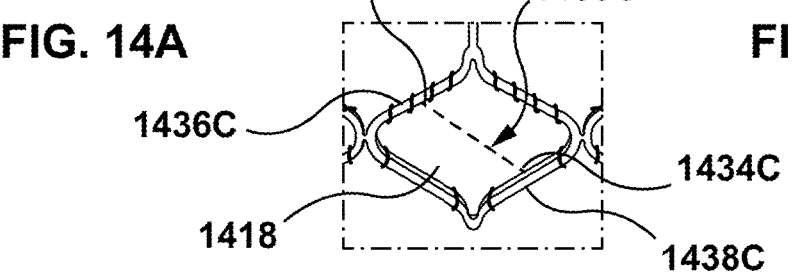
FIG. 14C is an enlarged view of a side opening of a transcatheter heart valve prosthesis according to another embodiment hereof, wherein a skirt-reinforcement member extends in an angled orientation.

In another embodiment depicted in FIG. 14C, a first end 1432C of a skirt-reinforcement member 1430C is circumferentially offset from a second end 1434C of the skirt-reinforcement member 1430C such that the skirt-reinforcement member 1430C is angled relative to the axis LA of the frame. The first end 1432C of the skirt-reinforcement member 1430C is attached to a first edge 1436C defining the respective side opening 1418 and the second end 1434C of the skirt-reinforcement member 1430C is attached to a second or opposing edge 1438C defining the respective side opening 1418. Adjacent skirt-reinforcement members 1430C may have alternating orientations (i.e., diagonally downward and diagonally upward) such that the skirt-reinforcement members 1430C collectively circumscribe the frame in a zig-zag configuration. However, adjacent skirt-reinforcement members 1430C are not required to have alternating orientations and further each side opening 1418 is not required to include a skirt reinforcement member as described above.

Similar to the skirt-reinforcement members 1030, 1130, 1230 described above, the skirt-reinforcement members 1430, 1430B, 1430C may include a strip of fabric or tissue in addition to a filament or strand of suture that forms a plurality of stitches. In addition, an alternative to the plurality of skirt-reinforcement members 1430, the transcatheter heart valve prosthesis 1400 may include a continuous band or ring that extends 360° around an outer surface of the frame 1402. The ring would be attached to the skirt 1412 and may be the same as the skirt-reinforcement member 1330 described above. The ring would be positioned over the same row of side openings 1418 as shown with respect to the skirt-reinforcement members 1430 in FIG. 14.

Figure 15:
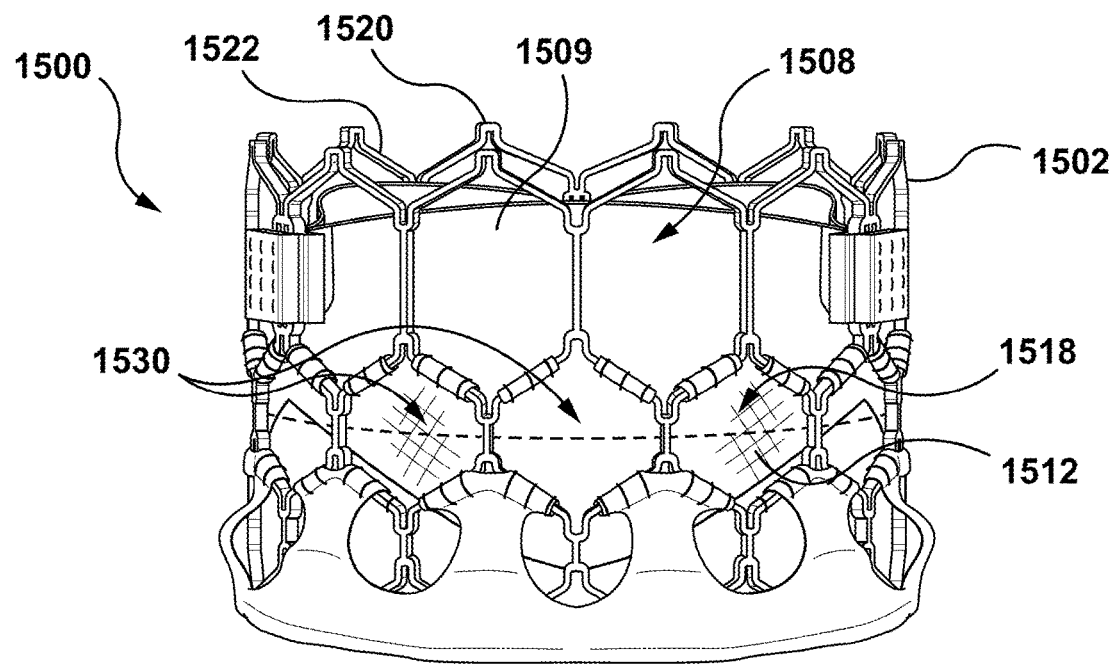
FIG. 15 depicts a perspective view of a transcatheter heart valve prosthesis in accordance with another aspect of the disclosure, wherein the frame further includes a plurality of skirt-reinforcement members.

FIG. 15 depicts a perspective view of a transcatheter heart valve prosthesis 1500 in accordance with another aspect of the disclosure. The transcatheter heart valve prosthesis 1500 includes a stent or frame 1502 and a prosthetic valve component 1508 including at least one leaflet disposed within and secured to the frame 1502. The frame 1502 includes a plurality of crowns 1520 and a plurality of struts 1522 with each crown 1520 being formed between a pair of opposing struts 1522. Each crown 1520 is a curved segment or bend extending between opposing struts 1522. The frame 1502 is tubular, with the plurality of side openings 1518 being defined by edges of the plurality of crowns 1520 and the plurality of struts 1522. In an embodiment, the plurality of side openings 1518 may be substantially hexagonal-shaped.

The frame 1502 includes a skirt 1512 coupled to a surface thereof. More particularly, the skirt 1512 is coupled to an inner surface of the frame 1502 to line a portion thereof. Alternatively, the skirt 1512 may be coupled to an outer surface of the frame 1502 to enclose a portion thereof as would be known to one of ordinary skill in the art of prosthetic valve construction. The skirt 1512 may be formed from the same materials described above with respect to the skirt 112.

The prosthetic valve component 1508 of the transcatheter heart valve prosthesis 1500 is capable of regulating flow therethrough via valve leaflets that may form a replacement valve. FIG. 15 illustrates an exemplary prosthetic valve component having three leaflets 1509, although a single leaflet or bicuspid leaflet configuration may alternatively be used in embodiments hereof. As described above with respect to the prosthetic valve component 108, when deployed in situ, the prosthetic valve component 1508 in a closed state is configured to block blood flow in one direction to regulate blood flow through a central lumen of the frame 1502.

The valve leaflets 1509 may be attached to the skirt 1512. The skirt 1512 may billow during valve opening and closing in situ, and the leaflets 1509 may contact the skirt 1512. Such billowing may undesirably result in contact between the skirt 1512 and the leaflets 1509 of the transcatheter heart valve prosthesis 1500. If the leaflets 1509 of the transcatheter heart valve prosthesis 1500 contact the skirt 1512 during opening and closing, such contact may cause early leaflet tissue abrasion as well as early skirt abrasion. Additionally, the greater relative motion between the skirt 1512 and the frame 1502 may further induce early skirt abrasion. Thus, the transcatheter heart valve prosthesis 1500 further includes a plurality of skirt-reinforcement members 1530. As described above with respect to the skirt-reinforcement members 730 described above, the skirt-reinforcement members 1530 reinforce the material of the skirt 1512 that spans across the side openings 1518 of the frame 1502 to limit the radial motion or billowing of the skirt material, thereby minimizing risk of damage to both the skirt 1512 and the leaflets 1509.

In the embodiment of FIG. 15, the frame 1502 includes a row of side openings 1518 around a circumference thereof and a skirt-reinforcement member 1530 spans across or extends over each side opening 1518 of the row of side openings 1518 around the circumference of the frame 1502. However, it is not required that a skirt-reinforcement member 1530 be utilized on every side opening 1518 of the row of side openings 1518 around the circumference of the frame 1502. Rather, a skirt-reinforcement member 1530 may be utilized only on the side openings 1518 having skirt material that may come into contact with leaflets 1509 when the leaflets are opening and closing in situ. At least one side opening 1518 must include a skirt-reinforcement member 1530 according to an aspect of the present disclosure. Further, the placement of the skirt-reinforcement members 1530 is exemplary only and the skirt-reinforcement members 1530 may be disposed on side openings 1518 of different rows from that depicted on FIG. 15.

Figure 15A:
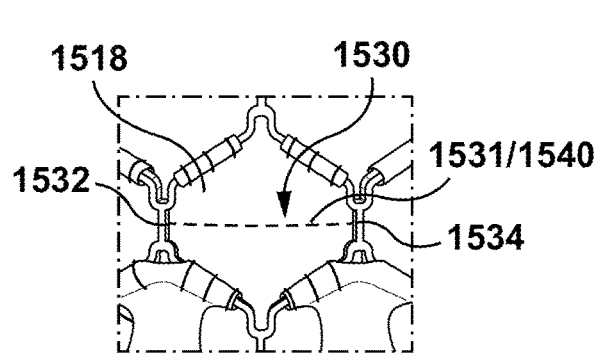
FIG. 15A is an enlarged view of a side opening of the transcatheter heart valve prosthesis of FIG. 15.

FIG. 15A is an enlarged view of a side opening 1518 of the frame 1502 that includes a skirt-reinforcement member 1530. Each skirt-reinforcement member 1530 spans a side opening 1518 from a first crown or strut edge defining the at least one side opening 1518 to a second crown or strut edge defining the at least one side opening 1518. In the embodiments of FIGS. 15-15A, the skirt-reinforcement members 1530 are the same as the skirt-reinforcement members 730. Each skirt-reinforcement member 1530 is a filament or strand 1531 of suture that forms a plurality of stitches 1540. The skirt-reinforcement member 1530 is directly attached to the skirt 1512 along an unsupported portion of the skirt 1512 that spans the respective side opening 1518. A plurality of stitches 1540 of the skirt-reinforcement member 1530 extends or weaves through the material of the skirt 1512 to ensure that the skirt-reinforcement member 1530 applies tension to the skirt 1512 and thereby prevents undesired billowing of the skirt material. The first and second ends 1532, 1534 of the skirt-reinforcement member 1530 are attached to the frame 1502 such that the skirt-reinforcement member 1530 has sufficient tension along its length to minimize radial movement of the skirt 1512 throughout the cardiac cycle.

Figure 15B:
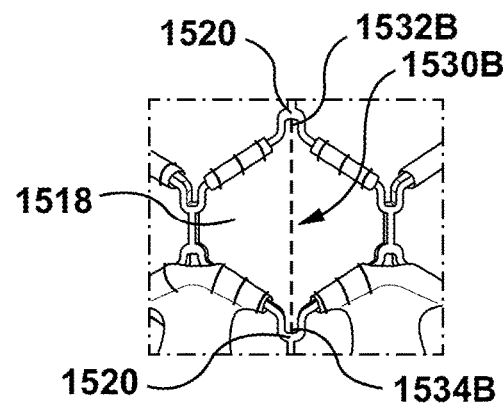
FIG. 15B is an enlarged view of a side opening of a transcatheter heart valve prosthesis according to another embodiment hereof, wherein a skirt-reinforcement member extends in a vertical orientation.

In FIGS. 15 and 15A, the skirt-reinforcement member 1530 extends in a horizontal orientation over the side opening 1518 in a center or middle thereof. However, other placements of the skirt-reinforcement members are contemplated herein. For example, in the embodiment depicted in FIG. 15B, a skirt-reinforcement member 1530B extends in a vertical orientation over the side opening 1518 in a center or middle thereof. A first end 1532B of a skirt-reinforcement member 1530B is longitudinally offset from a second end 1534B of the skirt-reinforcement member 1530B such that the skirt-reinforcement member 1530B is parallel or substantially parallel relative to the axis LA of the frame. The first end 1532B of the skirt-reinforcement member 1530B is attached to a first crown 1520B defining the respective side opening 1518 and the second end 1534B of the skirt-reinforcement member 1530 is attached to a second or opposing crown 1520B defining the respective side opening 1518 such that the skirt-reinforcement member 1530B spans vertically across the side opening 1518.

Figure 15C:
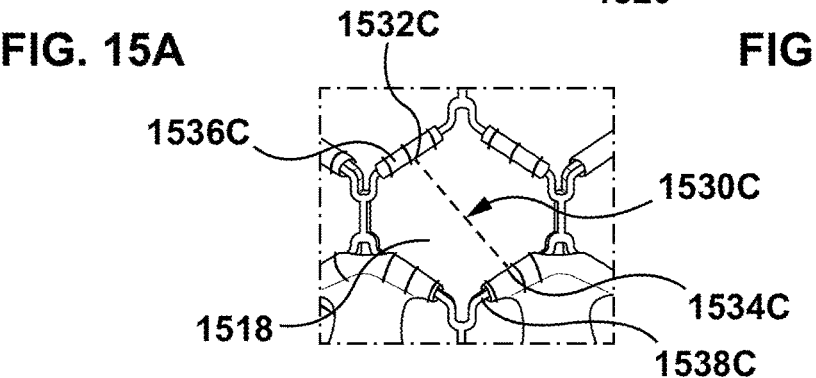
FIG. 15C is an enlarged view of a side opening of a transcatheter heart valve prosthesis according to another embodiment hereof, wherein a skirt-reinforcement member extends in an angled orientation.

In another embodiment depicted in FIG. 15C, a first end 1532C of a skirt-reinforcement member 1530C is circumferentially offset from a second end 1534C of the skirt-reinforcement member 1530C such that the skirt-reinforcement member 1530C is angled relative to the axis LA of the frame. The first end 1532C of the skirt-reinforcement member 1530C is attached to a first edge 1536C defining the respective side opening 1518 and the second end 1534C of the skirt-reinforcement member 1530C is attached to a second or opposing edge 1538C defining the respective side opening 1518. Adjacent skirt-reinforcement members 1530C may have alternating orientations (i.e., diagonally downward and diagonally upward) such that the skirt-reinforcement members 1530C collectively circumscribe the frame in a zig-zag configuration. However, adjacent skirt-reinforcement members 1530C are not required to have alternating orientations and further each side opening 1518 is not required to include a skirt reinforcement member as described above.

Similar to the skirt-reinforcement members 1030, 1130, 1230 described above, the skirt-reinforcement members 1530, 1530B, 1530C may include a strip of fabric or tissue in addition to a filament or strand of suture that forms a plurality of stitches. In addition, an alternative to the plurality of skirt-reinforcement members 1530, the transcatheter heart valve prosthesis 1500 may include a continuous band or ring that extends 360° around an outer surface of the frame 1502. The ring would be attached to the skirt 1512 and may be the same as the skirt-reinforcement member 1330 described above. The ring would be positioned over the same row of side openings 1518 as shown with respect to the skirt-reinforcement members 1530 in FIG. 15.

Figure 16:
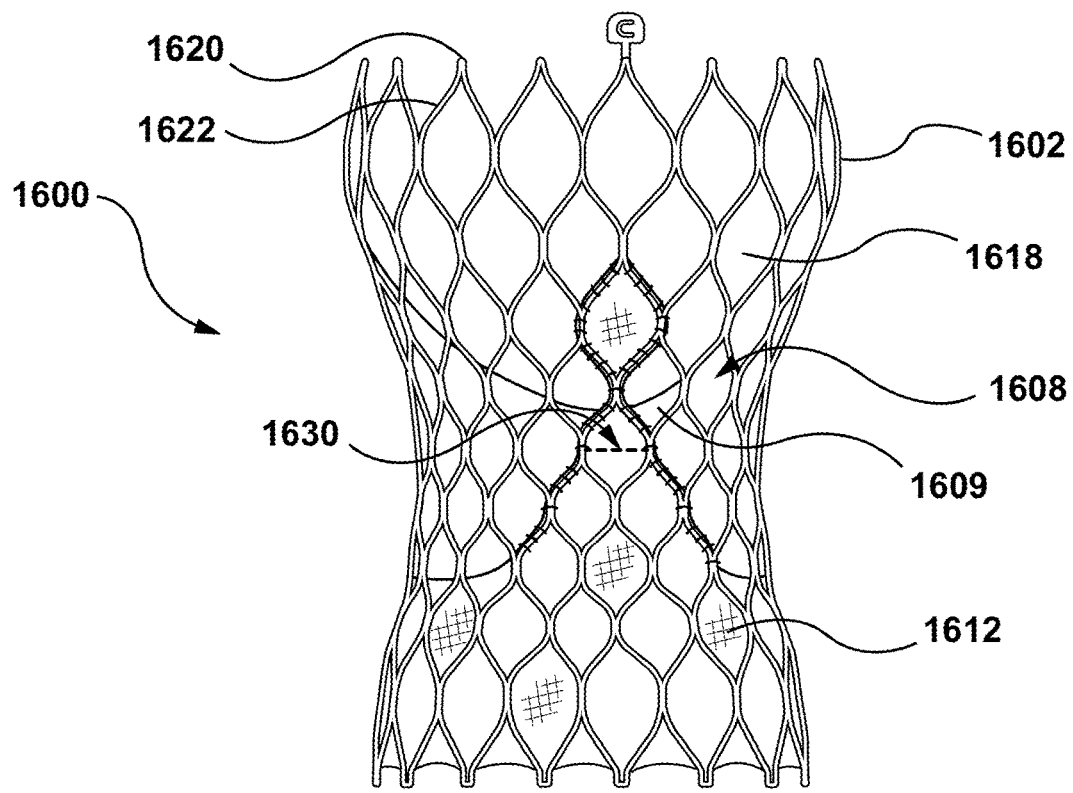
FIG. 16 depicts a perspective view of a transcatheter heart valve prosthesis in accordance with another aspect of the disclosure, wherein the frame further includes a plurality of skirt-reinforcement members.

FIG. 16 depicts a perspective view of a transcatheter heart valve prosthesis 1600 in accordance with another aspect of the disclosure. The transcatheter heart valve prosthesis 1600 includes a stent or frame 1602 and a prosthetic valve component 1608 including at least one leaflet disposed within and secured to the frame 1602. The frame 1602 includes a plurality of crowns 1620 and a plurality of struts 1622 with each crown 1620 being formed between a pair of opposing struts 1622. Each crown 1620 is a curved segment or bend extending between opposing struts 1622. The frame 1602 is tubular, with the plurality of side openings 1618 being defined by edges of the plurality of crowns 1620 and the plurality of struts 1622. In an embodiment, the plurality of side openings 1618 may be substantially diamond-shaped.

The frame 1602 includes a skirt 1612 coupled to a surface thereof. More particularly, the skirt 1612 is coupled to an inner surface of the frame 1602 to line a portion thereof. Alternatively, the skirt 1612 may be coupled to an outer surface of the frame 1602 to enclose a portion thereof as would be known to one of ordinary skill in the art of prosthetic valve construction. The skirt 1612 may be formed from the same materials described above with respect to the skirt 112.

The prosthetic valve component 1608 of the transcatheter heart valve prosthesis 1600 is capable of regulating flow therethrough via valve leaflets that may form a replacement valve. FIG. 16 illustrates an exemplary prosthetic valve component having three leaflets 1609, although a single leaflet or bicuspid leaflet configuration may alternatively be used in embodiments hereof. As described above with respect to the prosthetic valve component 108, when deployed in situ, the prosthetic valve component 1608 in a closed state is configured to block blood flow in one direction to regulate blood flow through a central lumen of the frame 1602.

The valve leaflets 1609 may be attached to the skirt 1612. The skirt 1612 may billow during valve opening and closing in situ, and the leaflets 1609 may contact the skirt 1612. Such billowing may undesirably result in contact between the skirt 1612 and the leaflets 1609 of the transcatheter heart valve prosthesis 1600. If the leaflets 1609 of the transcatheter heart valve prosthesis 1600 contact the skirt 1612 during opening and closing, such contact may cause early leaflet tissue abrasion as well as early skirt abrasion. Additionally, the greater relative motion between the skirt 1612 and the frame 1602 may further induce early skirt abrasion. Thus, the transcatheter heart valve prosthesis 1600 further includes a plurality of skirt-reinforcement members 1630. As described above with respect to the skirt-reinforcement members 730 described above, the skirt-reinforcement members 1630 reinforce the material of the skirt 1612 that spans across the side openings 1618 of the frame 1602 to limit the radial motion or billowing of the skirt material, thereby minimizing risk of damage to both the skirt 1612 and the leaflets 1609.

In the embodiment of FIG. 16, the frame 1602 includes exactly three skirt-reinforcement members 1630 (although two skirt-reinforcement members are obscured from view). The skirt-reinforcement members 1630 are disposed at the leaflet commissures and are spaced at substantially equal intervals around a circumference of the frame 102. However, the placement of the skirt-reinforcement members 1630 is exemplary only and the skirt-reinforcement members 1630 may be disposed at different side openings 1618 from those depicted on FIG. 16.

Figure 16A:
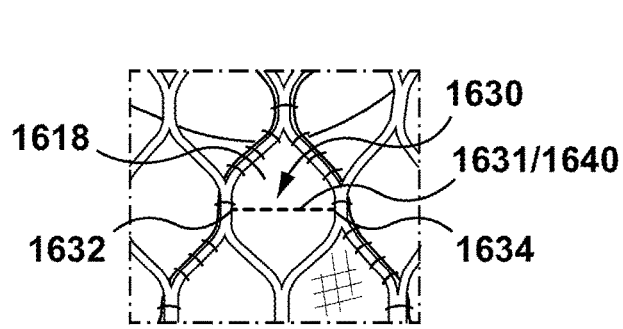
FIG. 16A is an enlarged view of a side opening of the transcatheter heart valve prosthesis of FIG. 16.

FIG. 16A is an enlarged view of a side opening 1618 of the frame 1602 that includes a skirt-reinforcement member 1630. Each skirt-reinforcement member 1630 spans a side opening 1618 from a first crown or strut edge defining the at least one side opening 1618 to a second crown or strut edge defining the at least one side opening 1618. In the embodiments of FIGS. 16-16A, the skirt-reinforcement members 1630 are the same as the skirt-reinforcement members 730. Each skirt-reinforcement member 1630 is a filament or strand 1631 of suture that forms a plurality of stitches 1640. The skirt-reinforcement member 1630 is directly attached to the skirt 1612 along an unsupported portion of the skirt 1612 that spans the respective side opening 1618. A plurality of stitches 1640 of the skirt-reinforcement member 1630 extends or weaves through the material of the skirt 1612 to ensure that the skirt-reinforcement member 1630 applies tension to the skirt 1612 and thereby prevents undesired billowing of the skirt material. The first and second ends 1632, 1634 of the skirt-reinforcement member 1630 are attached to the frame 1602 such that the skirt-reinforcement member 1630 has sufficient tension along its length to minimize radial movement of the skirt 1612 throughout the cardiac cycle.

Figure 16B:
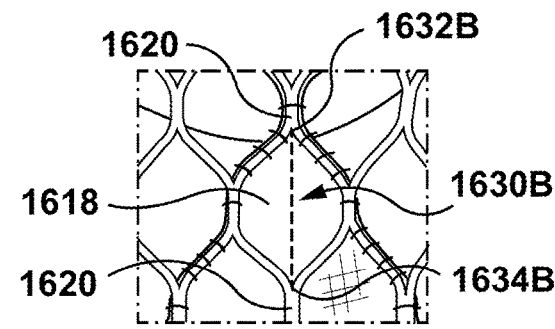
FIG. 16B is an enlarged view of a side opening of a transcatheter heart valve prosthesis according to another embodiment hereof, wherein a skirt-reinforcement member extends in a vertical orientation.

In FIGS. 16 and 16A, the skirt-reinforcement member 1630 extends in a horizontal orientation over the side opening 1618 in a center or middle thereof. However, other placements of the skirt-reinforcement members are contemplated herein. For example, in the embodiment depicted in FIG. 16B, a skirt-reinforcement member 1630B extends in a vertical orientation over the side opening 1618 in a center or middle thereof. A first end 1632B of a skirt-reinforcement member 1630B is longitudinally offset from a second end 1634B of the skirt-reinforcement member 1630B such that the skirt-reinforcement member 1630B is parallel or substantially parallel relative to the axis LA of the frame. The first end 1632B of the skirt-reinforcement member 1630B is attached to a first crown 1620B defining the respective side opening 1618 and the second end 1634B of the skirt-reinforcement member 1630 is attached to a second or opposing crown 1620B defining the respective side opening 1618 such that the skirt-reinforcement member 1630B spans vertically across the side opening 1618.

Figure 16C:
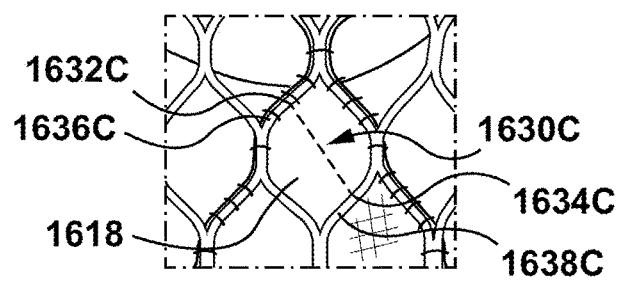
FIG. 16C is an enlarged view of a side opening of a transcatheter heart valve prosthesis according to another embodiment hereof, wherein a skirt-reinforcement member extends in an angled orientation.

In another embodiment depicted in FIG. 16C, a first end 1632C of a skirt-reinforcement member 1630C is circumferentially offset from a second end 1634C of the skirt-reinforcement member 1630C such that the skirt-reinforcement member 1630C is angled relative to the axis LA of the frame. The first end 1632C of the skirt-reinforcement member 1630C is attached to a first edge 1636C defining the respective side opening 1618 and the second end 1634C of the skirt-reinforcement member 1630C is attached to a second or opposing edge 1638C defining the respective side opening 1618.

Similar to the skirt-reinforcement members 1030, 1130, 1230 described above, the skirt-reinforcement members 1630, 1630B, 1630C may include a strip of fabric or tissue in addition to a filament or strand of suture that forms a plurality of stitches. In addition, an alternative to the plurality of skirt-reinforcement members 1630, the transcatheter heart valve prosthesis 1600 may include a continuous band or ring that extends 360° around an outer surface of the frame 1602. The ring would be attached to the skirt 1612 and may be the same as the skirt-reinforcement member 1330 described above.

Figure 17:
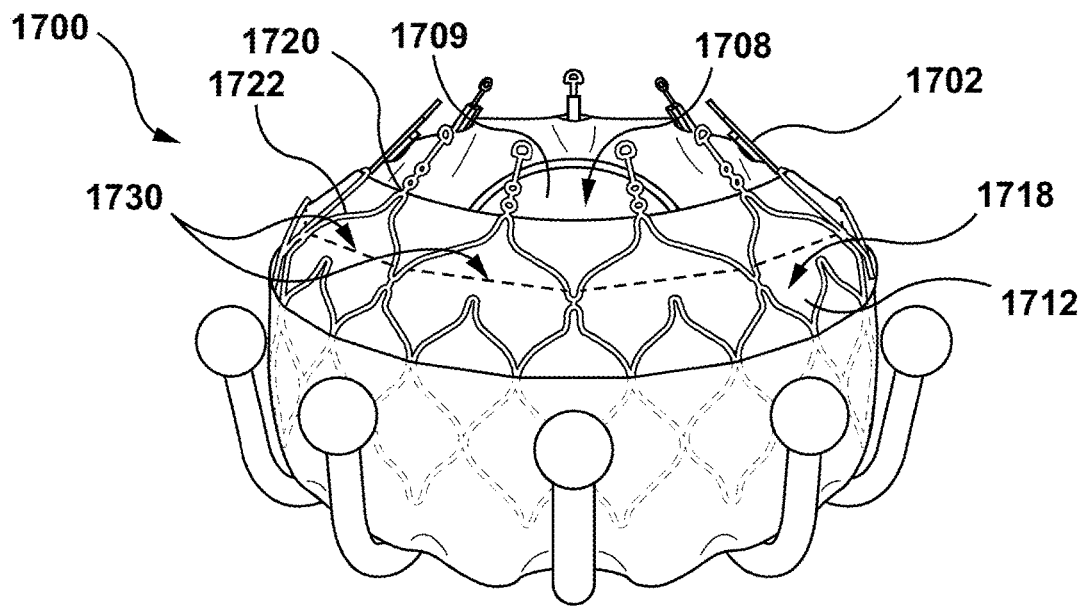
FIG. 17 depicts a perspective view of a transcatheter heart valve prosthesis in accordance with another aspect of the disclosure, wherein the frame further includes a plurality of skirt-reinforcement members.

FIG. 17 depicts a perspective view of a transcatheter heart valve prosthesis 1700 in accordance with another aspect of the disclosure. The transcatheter heart valve prosthesis 1700 includes a stent or frame 1702 and a prosthetic valve component 1708 including at least one leaflet disposed within and secured to the frame 1702. The frame 1702 includes a plurality of crowns 1720 and a plurality of struts 1722 with each crown 1720 being formed between a pair of opposing struts 1722. Each crown 1720 is a curved segment or bend extending between opposing struts 1722. The frame 1702 is tubular, with the plurality of side openings 1718 being defined by edges of the plurality of crowns 1720 and the plurality of struts 1722. In an embodiment, the plurality of side openings 1718 may be substantially heart-shaped, with each side opening 1718 being formed by six struts 1722 and six crowns 1720.

The frame 1702 includes a skirt 1712 coupled to a surface thereof. More particularly, the skirt 1712 is coupled to an inner surface of the frame 1702 to line a portion thereof. Alternatively, the skirt 1712 may be coupled to an outer surface of the frame 1702 to enclose a portion thereof as would be known to one of ordinary skill in the art of prosthetic valve construction. The skirt 1712 may be formed from the same materials described above with respect to the skirt 112.

The prosthetic valve component 1708 of the transcatheter heart valve prosthesis 1700 is capable of regulating flow therethrough via valve leaflets that may form a replacement valve. FIG. 17 illustrates an exemplary prosthetic valve component having three leaflets 1709, although a single leaflet or bicuspid leaflet configuration may alternatively be used in embodiments hereof. As described above with respect to the prosthetic valve component 108, when deployed in situ, the prosthetic valve component 1708 in a closed state is configured to block blood flow in one direction to regulate blood flow through a central lumen of the frame 1702.

The valve leaflets 1709 may be attached to the skirt 1712. The skirt 1712 may billow during valve opening and closing in situ, and the leaflets 1709 may contact the skirt 1712. Such billowing may undesirably result in contact between the skirt 1712 and the leaflets 1709 of the transcatheter heart valve prosthesis 1700. If the leaflets 1709 of the transcatheter heart valve prosthesis 1700 contact the skirt 1712 during opening and closing, such contact may cause early leaflet tissue abrasion as well as early skirt abrasion. Additionally, the greater relative motion between the skirt 1712 and the frame 1702 may further induce early skirt abrasion. Thus, the transcatheter heart valve prosthesis 1700 further includes a plurality of skirt-reinforcement members 1730. As described above with respect to the skirt-reinforcement members 730 described above, the skirt-reinforcement members 1730 reinforce the material of the skirt 1712 that spans across the side openings 1718 of the frame 1702 to limit the radial motion or billowing of the skirt material, thereby minimizing risk of damage to both the skirt 1712 and the leaflets 1709.

In the embodiment of FIG. 17, the frame 1702 includes a row of side openings 1718 around a circumference thereof and a skirt-reinforcement member 1730 spans across or extends over each side opening 1718 of the row of side openings 1718 around the circumference of the frame 1702. However, it is not required that a skirt-reinforcement member 1730 be utilized on every side opening 1718 of the row of side openings 1718 around the circumference of the frame 1702. Rather, a skirt-reinforcement member 1730 may be utilized only on the side openings 1718 having skirt material that may come into contact with leaflets 1709 when the leaflets are opening and closing in situ. At least one side opening 1718 must include a skirt-reinforcement member 1730 according to an aspect of the present disclosure. Further, the placement of the skirt-reinforcement members 1730 is exemplary only and the skirt-reinforcement members 1730 may be disposed on side openings 1718 of different rows from that depicted on FIG. 17.

Figure 17A:
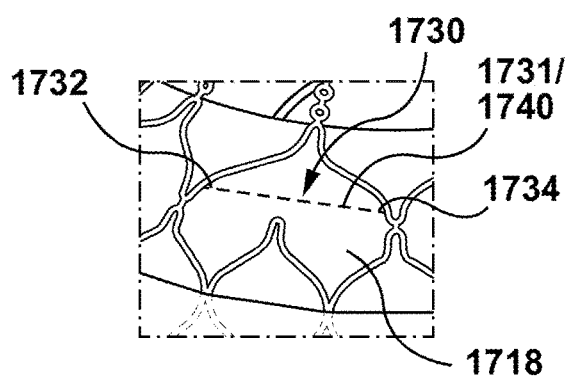
FIG. 17A is an enlarged view of a side opening of the transcatheter heart valve prosthesis of FIG. 17.

FIG. 17A is an enlarged view of a side opening 1718 of the frame 1702 that includes a skirt-reinforcement member 1730. Each skirt-reinforcement member 1730 spans a side opening 1718 from a first crown or strut edge defining the at least one side opening 1718 to a second crown or strut edge defining the at least one side opening 1718. In the embodiments of FIGS. 17-17A, the skirt-reinforcement members 1730 are the same as the skirt-reinforcement members 730. Each skirt-reinforcement member 1730 is a filament or strand 1731 of suture that forms a plurality of stitches 1740. The skirt-reinforcement member 1730 is directly attached to the skirt 1712 along an unsupported portion of the skirt 1712 that spans the respective side opening 1718. A plurality of stitches 1740 of the skirt-reinforcement member 1730 extends or weaves through the material of the skirt 1712 to ensure that the skirt-reinforcement member 1730 applies tension to the skirt 1712 and thereby prevents undesired billowing of the skirt material. The first and second ends 1732, 1734 of the skirt-reinforcement member 1730 are attached to the frame 1702 such that the skirt-reinforcement member 1730 has sufficient tension along its length to minimize radial movement of the skirt 1712 throughout the cardiac cycle.

Figure 17B:
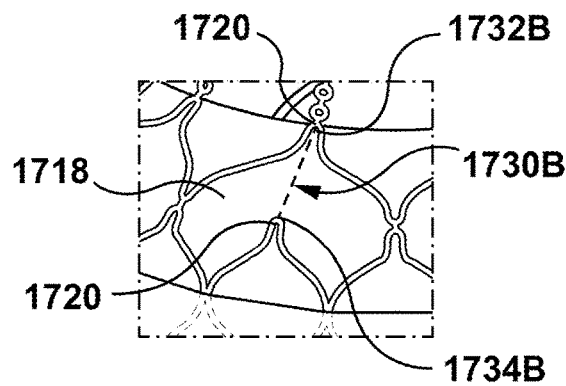
FIG. 17B is an enlarged view of a side opening of a transcatheter heart valve prosthesis according to another embodiment hereof, wherein a skirt-reinforcement member extends in a vertical orientation.

In FIGS. 17 and 17A, the skirt-reinforcement member 1730 extends in a horizontal orientation over the side opening 1718. However, other placements of the skirt-reinforcement members are contemplated herein. For example, in the embodiment depicted in FIG. 17B, a skirt-reinforcement member 1730B extends in a vertical orientation over the side opening 1718 in a center or middle thereof. A first end 1732B of a skirt-reinforcement member 1730B is longitudinally offset from a second end 1734B of the skirt-reinforcement member 1730B such that the skirt-reinforcement member 1730B is parallel or substantially parallel relative to the axis LA of the frame. The first end 1732B of the skirt-reinforcement member 1730B is attached to a first crown 1720B defining the respective side opening 1718 and the second end 1734B of the skirt-reinforcement member 1730 is attached to a second or opposing crown 1720B defining the respective side opening 1718 such that the skirt-reinforcement member 1730B spans vertically across the side opening 1718.

Figure 17C:
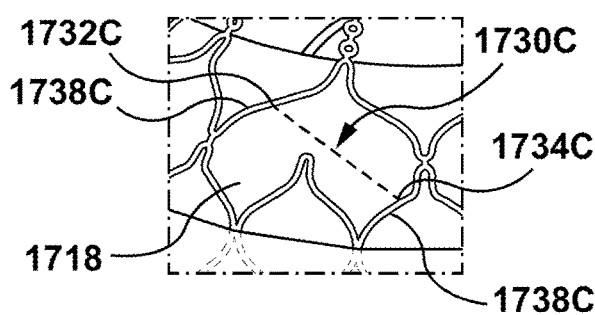
FIG. 17C is an enlarged view of a side opening of a transcatheter heart valve prosthesis according to another embodiment hereof, wherein a skirt-reinforcement member extends in an angled orientation.

In another embodiment depicted in FIG. 17C, a first end 1732C of a skirt-reinforcement member 1730C is circumferentially offset from a second end 1734C of the skirt-reinforcement member 1730C such that the skirt-reinforcement member 1730C is angled relative to the axis LA of the frame. The first end 1732C of the skirt-reinforcement member 1730C is attached to a first edge 1736C defining the respective side opening 1718 and the second end 1734C of the skirt-reinforcement member 1730C is attached to a second or opposing edge 1738C defining the respective side opening 1718. Adjacent skirt-reinforcement members 1730C may have alternating orientations (i.e., diagonally downward and diagonally upward) such that the skirt-reinforcement members 1730C collectively circumscribe the frame in a zig-zag configuration. However, adjacent skirt-reinforcement members 1730C are not required to have alternating orientations and further each side opening 1718 is not required to include a skirt reinforcement member as described above.

Figure 17D:
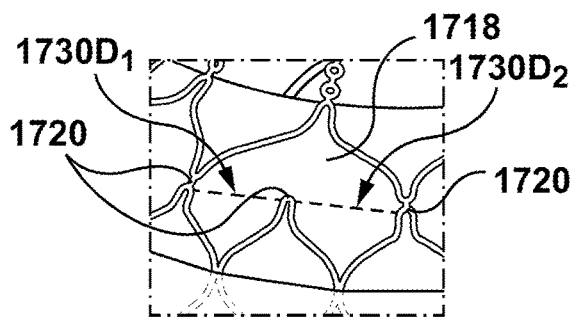
FIG. 17D is an enlarged view of a side opening of a transcatheter heart valve prosthesis according to another embodiment hereof, wherein two skirt-reinforcement members are disposed over a single side opening of the transcatheter valve prosthesis.

In another embodiment depicted in FIG. 17D, two skirt-reinforcement members $1730D_1$, $1730D_2$ extend in a horizontal orientation over a single side opening 1718. Each skirt-reinforcement member $1730D_1$, $1730D_2$ spans the side opening 1718 from a first crown or strut edge defining the side opening 1718 to a second crown or strut edge defining the at least one side opening 1718. In the depicted embodiment, each skirt-reinforcement member $1730D_1$, $1730D_2$ has a first end attached to a first crown 1720 defining the respective side opening 1718 and a second end attached to a second or opposing crown 1720 defining the respective side opening 1718. In the depicted embodiment, each skirt-reinforcement member $1730D_1$, $1730D_2$ are aligned with each other and have the same orientation, but the placement of the skirt-reinforcement members $11730D_1$, $1730D_2$ are exemplary only and the skirt-reinforcement members $1730D_1$, $1730D_2$ may be disposed in different orientations from that depicted on FIG. 17.

Similar to the skirt-reinforcement members 1030, 1130, 1230 described above, the skirt-reinforcement members 1730, 1730B, 1730C may include a strip of fabric or tissue in addition to a filament or strand of suture that forms a plurality of stitches. In addition, an alternative to the plurality of skirt-reinforcement members 1730, the transcatheter heart valve prosthesis 1700 may include a continuous band or ring that extends 360° around an outer surface of the frame 1702. The ring would be attached to the skirt 1712 and may be the same as the skirt-reinforcement member 1330 described above. The ring would be positioned over the same row of side openings 1718 as shown with respect to the skirt-reinforcement members 1730 in FIG. 17.

Figure 18:
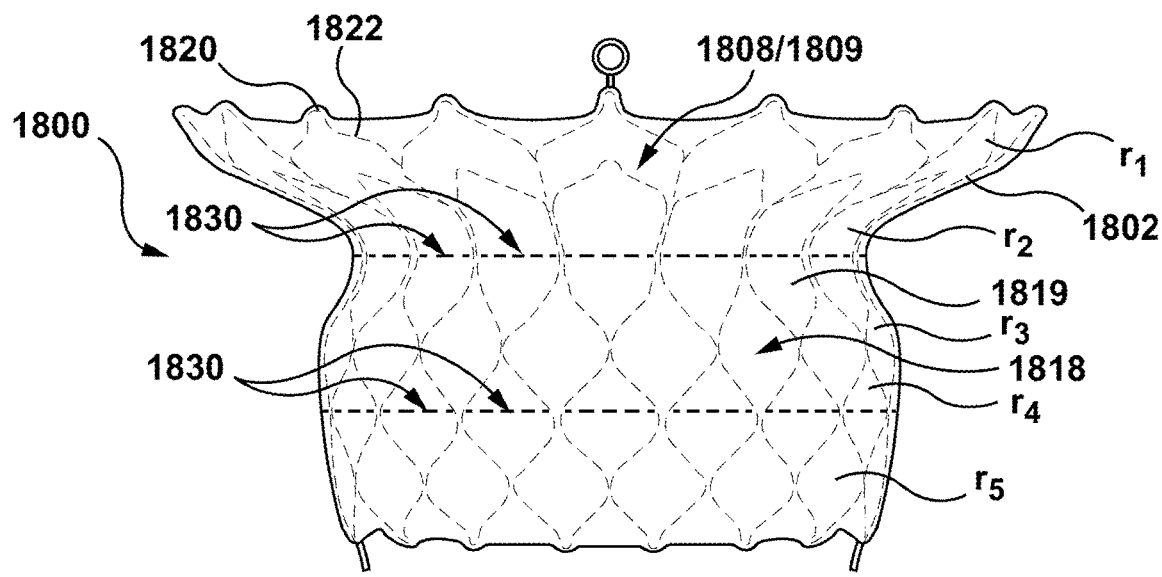
FIG. 18 depicts a perspective view of a transcatheter heart valve prosthesis in accordance with another aspect of the disclosure, wherein the frame further includes a plurality of skirt-reinforcement members.

FIG. 18 depicts a perspective view of a transcatheter heart valve prosthesis 1800 in accordance with another aspect of the disclosure. The transcatheter heart valve prosthesis 1800 includes a stent or frame 1802 and a prosthetic valve component 1808 including at least one leaflet disposed within and secured to the frame 1802. The frame 1802 includes a plurality of crowns 1820 and a plurality of struts 1822 with each crown 1820 being formed between a pair of opposing struts 1822. Each crown 1820 is a curved segment or bend extending between opposing struts 1822. The frame 1802 is tubular, with the plurality of side openings 1818 being defined by edges of the plurality of crowns 1820 and the plurality of struts 1822. The frame 1802 includes five rows of side openings 1818, labeled as rows $r_1$, $r_2$, $r_3$, $r_4$, $r_5$ on FIG. 18. In an embodiment, the plurality of side openings 1818 on each of rows $r_3$, $r_4$, $r_5$, may be substantially diamond-shaped, while the side openings 1818 on row $r_2$ are each defined by five struts 1822 and the side openings 1818 on row $r_1$ are each defined by six struts 1822.

The frame 1802 includes a skirt 1812 coupled to a surface thereof. More particularly, the skirt 1812 is coupled to an inner surface of the frame 1802 to line a portion thereof. Alternatively, the skirt 1812 may be coupled to an outer surface of the frame 1802 to enclose a portion thereof as would be known to one of ordinary skill in the art of prosthetic valve construction. The skirt 1812 may be formed from the same materials described above with respect to the skirt 112.

The prosthetic valve component 1808 of the transcatheter heart valve prosthesis 1800 is capable of regulating flow therethrough via valve leaflets that may form a replacement valve. FIG. 18 illustrates an exemplary prosthetic valve component having three leaflets 1809, although a single leaflet or bicuspid leaflet configuration may alternatively be used in embodiments hereof. As described above with respect to the prosthetic valve component 108, when deployed in situ, the prosthetic valve component 1808 in a closed state is configured to block blood flow in one direction to regulate blood flow through a central lumen of the frame 1802.

The valve leaflets 1809 may be attached to the skirt 1812. The skirt 1812 may billow during valve opening and closing in situ, and the leaflets 1809 may contact the skirt 1812. Such billowing may undesirably result in contact between the skirt 1812 and the leaflets 1809 of the transcatheter heart valve prosthesis 1800. If the leaflets 1809 of the transcatheter heart valve prosthesis 1800 contact the skirt 1812 during opening and closing, such contact may cause early leaflet tissue abrasion as well as early skirt abrasion. Additionally, the greater relative motion between the skirt 1812 and the frame 1802 may further induce early skirt abrasion. Thus, the transcatheter heart valve prosthesis 1800 further includes a plurality of skirt-reinforcement members 1830. As described above with respect to the skirt-reinforcement members 730 described above, the skirt-reinforcement members 1830 reinforce the material of the skirt 1812 that spans across the side openings 1818 of the frame 1802 to limit the radial motion or billowing of the skirt material, thereby minimizing risk of damage to both the skirt 1812 and the leaflets 1809.

In the embodiment of FIG. 18, a skirt-reinforcement member 1830 spans across or extends over each side opening 1818 of row $r_2$ of side openings 1818 around the circumference of the frame 1802 and as well as each side opening 1818 of row $r_4$ of side openings 1818 around the circumference of the frame 1802. However, it is not required that a skirt-reinforcement member 1830 be utilized on every side opening 1818 of the rows $r_2$, $r_4$ of the side openings 1818 around the circumference of the frame 1802. Rather, a skirt-reinforcement member 1830 may be utilized only on the side openings 1818 having skirt material that may come into contact with leaflets 1809 when the leaflets are opening and closing in situ. At least one side opening 1818 must include a skirt-reinforcement member 1830 according to an aspect of the present disclosure. Further, the placement of the skirt-reinforcement members 1830 on rows $r_2$, $r_4$ of side openings 1818 is exemplary only and the skirt-reinforcement members 1830 may be disposed on the side openings 1818 of different rows from those depicted on FIG. 18.

Figure 18A:
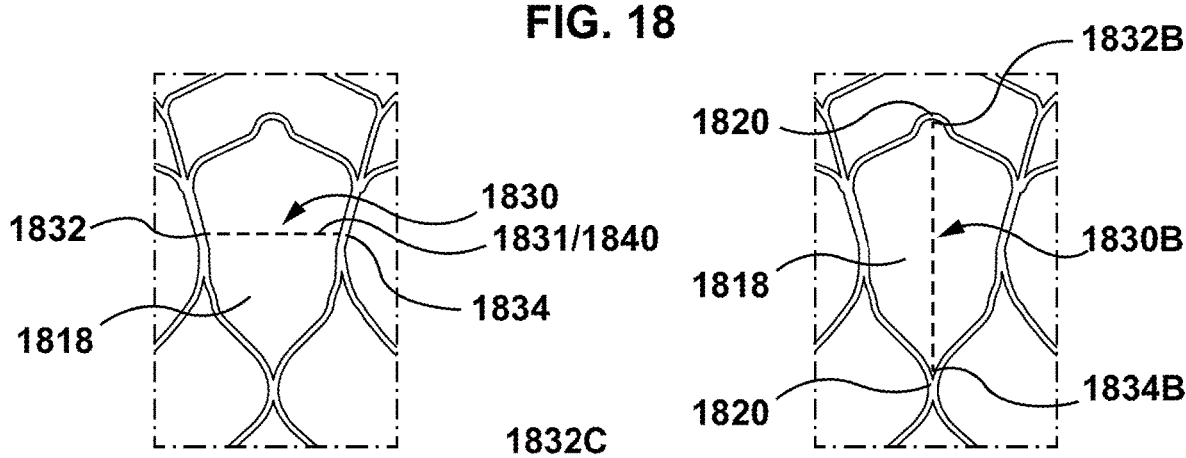
FIG. 18A is an enlarged view of a side opening of the transcatheter heart valve prosthesis of FIG. 18.

FIG. 18A is an enlarged view of a side opening 1818 of the frame 1802 that includes a skirt-reinforcement member 1830. Each skirt-reinforcement member 1830 spans a side opening 1818 from a first crown or strut edge defining the at least one side opening 1818 to a second crown or strut edge defining the at least one side opening 1818. In the embodiments of FIGS. 18-18A, the skirt-reinforcement members 1830 are the same as the skirt-reinforcement members 730. Each skirt-reinforcement member 1830 is a filament or strand 1831 of suture that forms a plurality of stitches 1840. The skirt-reinforcement member 1830 is directly attached to the skirt 1812 along an unsupported portion of the skirt 1812 that spans the respective side opening 1818. A plurality of stitches 1840 of the skirt-reinforcement member 1830 extends or weaves through the material of the skirt 1812 to ensure that the skirt-reinforcement member 1830 applies tension to the skirt 1812 and thereby prevents undesired billowing of the skirt material. The first and second ends 1832, 1834 of the skirt-reinforcement member 1830 are attached to the frame 1802 such that the skirt-reinforcement member 1830 has sufficient tension along its length to minimize radial movement of the skirt 1812 throughout the cardiac cycle.

Figure 18B:
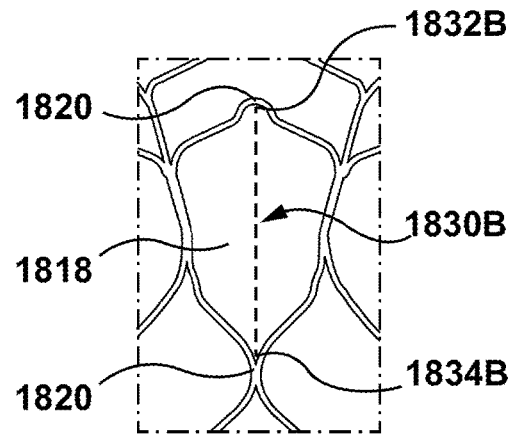
FIG. 18B is an enlarged view of a side opening of a transcatheter heart valve prosthesis according to another embodiment hereof, wherein a skirt-reinforcement member extends in a vertical orientation.

In FIGS. 18 and 18A, the skirt-reinforcement member 1830 extends in a horizontal orientation over the side opening 1818 in a center or middle thereof. However, other placements of the skirt-reinforcement members are contemplated herein. For example, in the embodiment depicted in FIG. 18B, a skirt-reinforcement member 1830B extends in a vertical orientation over the side opening 1818 in a center or middle thereof. A first end 1832B of a skirt-reinforcement member 1830B is longitudinally offset from a second end 1834B of the skirt-reinforcement member 1830B such that the skirt-reinforcement member 1830B is parallel or substantially parallel relative to the axis LA of the frame. The first end 1832B of the skirt-reinforcement member 1830B is attached to a first crown 1820B defining the respective side opening 1818 and the second end 1834B of the skirt-reinforcement member 1830 is attached to a second or opposing crown 1820B defining the respective side opening 1818 such that the skirt-reinforcement member 1830B spans vertically across the side opening 1818.

Figure 18C:
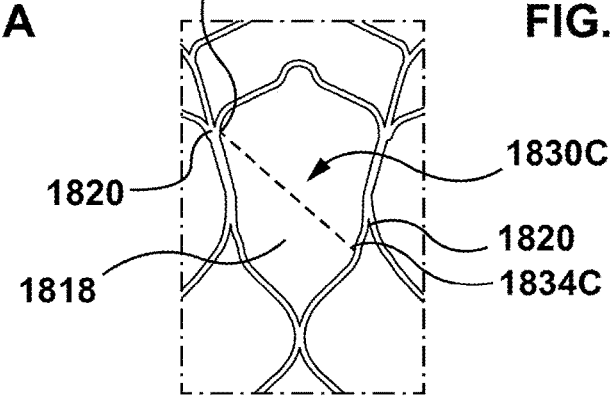
FIG. 18C is an enlarged view of a side opening of a transcatheter heart valve prosthesis according to another embodiment hereof, wherein a skirt-reinforcement member extends in an angled orientation.

In another embodiment depicted in FIG. 18C, a first end 1832C of a skirt-reinforcement member 1830C is circumferentially offset from a second end 1834C of the skirt-reinforcement member 1830C such that the skirt-reinforcement member 1830C is angled relative to the axis LA of the frame. The first end 1832C of the skirt-reinforcement member 1830C is attached to a first crown 1820, or a first edge, defining the respective side opening 1818 and the second end 1834C of the skirt-reinforcement member 1830C is attached to a second or opposing crown 1820, or a second or opposing edge, defining the respective side opening 1818. Adjacent skirt-reinforcement members 1830C may have alternating orientations (i.e., diagonally downward and diagonally upward) such that the skirt-reinforcement members 1830C collectively circumscribe the frame in a zig-zag configuration. However, adjacent skirt-reinforcement members 1830C are not required to have alternating orientations and further each side opening 1818 is not required to include a skirt reinforcement member as described above.

Similar to the skirt-reinforcement members 1030, 1130, 1230 described above, the skirt-reinforcement members 1830, 1830B, 1830C may include a strip of fabric or tissue in addition to a filament or strand of suture that forms a plurality of stitches. In addition, an alternative to the plurality of skirt-reinforcement members 1830, the transcatheter heart valve prosthesis 1800 may include a continuous band or ring that extends 360° around an outer surface of the frame 1802. The ring would be attached to the skirt 1812 and may be the same as the skirt-reinforcement member 1330 described above. The ring may be positioned over the same rows of side openings 1818 as shown with respect to the skirt-reinforcement members 1830 in FIG. 18.

Figures 19, 20:
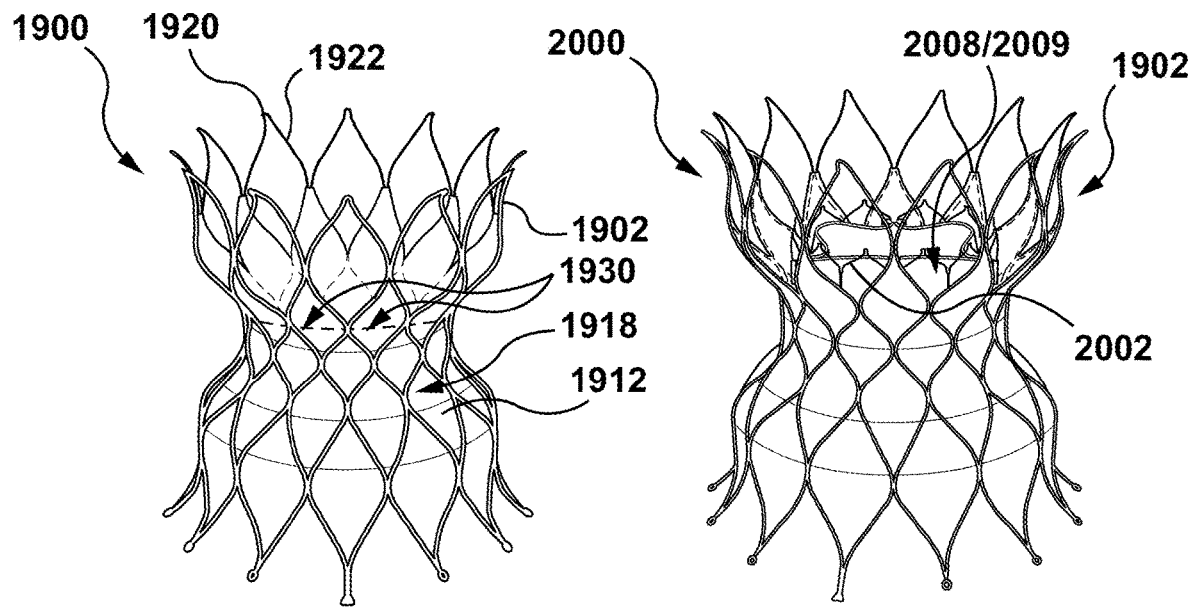
FIG. 19 depicts a perspective view of a docking prosthesis in accordance with another aspect of the disclosure, wherein a frame of the docking prosthesis includes a plurality of skirt-reinforcement members.
FIG. 20 is a perspective view of the docking prosthesis of FIG. 19 and a valve prosthesis disposed in the docking prosthesis.

Although embodiments above depict various transcatheter valve prostheses having at least one skirt-reinforcement member, the skirt-reinforcement members described herein may be applied to a docking prosthesis that is configured to receive a valve prosthesis therein. Such docking prostheses may include a skirt on a portion thereof that may come into contact with a leaflet of the valve prosthesis received therein when the leaflets are opening and closing in situ. For example, FIG. 19 depicts a perspective view of a docking prosthesis 1900 in accordance with another aspect of the disclosure. The docking prosthesis 1900 includes a stent or frame 1902. The frame 1902 includes a plurality of crowns 1920 and a plurality of struts 1922 with each crown 1920 being formed between a pair of opposing struts 1922. Each crown 1920 is a curved segment or bend extending between opposing struts 1922. The frame 1902 is tubular, with the plurality of side openings 1918 being defined by edges of the plurality of crowns 1920 and the plurality of struts 1922. In an embodiment, the plurality of side openings 1918 may be substantially diamond-shaped.

The frame 1902 includes a skirt 1912 coupled to a surface thereof. More particularly, the skirt 1912 is coupled to an inner surface of the frame 1902 to line a portion thereof. Alternatively, the skirt 1912 may be coupled to an outer surface of the frame 1902 to enclose a portion thereof. The skirt 1912 may be formed from the same materials described above with respect to the skirt 112.

With reference to FIG. 20, the docking prosthesis 1900 is configured to receive a valve prosthesis 2000 therein. The valve prosthesis 2000 includes a frame 2002 and a prosthetic valve component 2008 including at least one leaflet disposed within and secured to the frame 2002. The prosthetic valve component 2008 of the valve prosthesis 2000 is capable of regulating flow therethrough via valve leaflets that may form a replacement valve. The prosthetic valve component 2008 may have three leaflets 2009, although a single leaflet or bicuspid leaflet configuration may alternatively be used in embodiments hereof. As described above with respect to the prosthetic valve component 108, when deployed in situ, the prosthetic valve component 2008 in a closed state is configured to block blood flow in one direction to regulate blood flow through a central lumen of the frame 2002. The valve leaflets 2009 may be attached to the frame 2002.

The skirt 1912 of the docking prosthesis 1900 may billow during opening and closing of the leaflets 2009 in situ, and the leaflets 2009 may contact the skirt 1912. Such billowing may undesirably result in contact between the skirt 1912 of the docking prosthesis 1900 and the leaflets 2009 of the valve prosthesis 2000. If the leaflets 2009 contact the skirt 1912 during opening and closing, such contact may cause early leaflet tissue abrasion as well as early skirt abrasion. Additionally, the greater relative motion between the skirt 1912 and the frame 1902 may further induce early skirt abrasion. Thus, the docking prosthesis 1900 further includes a plurality of skirt-reinforcement members 1930. As described above with respect to the skirt-reinforcement members 730 described above, the skirt-reinforcement members 1930 reinforce the material of the skirt 1912 that spans across the side openings 1918 of the frame 1902 to limit the radial motion or billowing of the skirt material, thereby minimizing risk of damage to both the skirt 1912 and the leaflets 2009.

In the embodiment of FIG. 19, the frame 1902 includes a row of side openings 1918 around a circumference thereof and a skirt-reinforcement member 1930 spans across or extends over each side opening 1918 of the row of side openings 1918 around the circumference of the frame 1902. However, it is not required that a skirt-reinforcement member 1930 be utilized on every side opening 1918 of the row of side openings 1918 around the circumference of the frame 1902. Rather, a skirt-reinforcement member 1930 may be utilized only on the side openings 1918 having skirt material that may come into contact with leaflets 2009 when the leaflets are opening and closing in situ. At least one side opening 1918 must include a skirt-reinforcement member 1930 according to an aspect of the present disclosure. Further, the placement of the skirt-reinforcement members 1930 is exemplary only and the skirt-reinforcement members 1930 may be disposed on side openings 1918 of different rows from that depicted on FIG. 19.

Figures 19A, 19B:
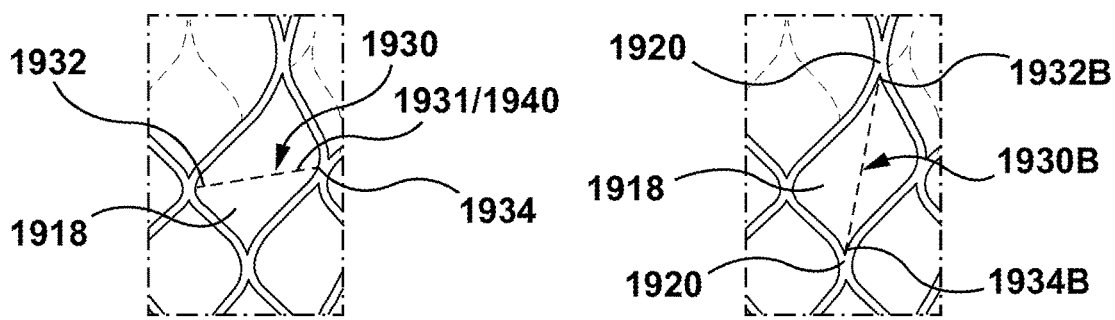
FIG. 19A is an enlarged view of a side opening of the docking prosthesis of FIG. 19.
FIG. 19B is an enlarged view of a side opening of a docking prosthesis according to another embodiment hereof, wherein a skirt-reinforcement member extends in a vertical orientation.

FIG. 19A is an enlarged view of a side opening 1918 of the frame 1902 that includes a skirt-reinforcement member 1930. Each skirt-reinforcement member 1930 spans a side opening 1918 from a first crown or strut edge defining the at least one side opening 1918 to a second crown or strut edge defining the at least one side opening 1918. In the embodiments of FIGS. 19-19A, the skirt-reinforcement members 1930 are the same as the skirt-reinforcement members 730. Each skirt-reinforcement member 1930 is a filament or strand 1931 of suture that forms a plurality of stitches 1940. The skirt-reinforcement member 1930 is directly attached to the skirt 1912 along an unsupported portion of the skirt 1912 that spans the respective side opening 1918. A plurality of stitches 1940 of the skirt-reinforcement member 1930 extends or weaves through the material of the skirt 1912 to ensure that the skirt-reinforcement member 1930 applies tension to the skirt 1912 and thereby prevents undesired billowing of the skirt material. The first and second ends 1932, 1934 of the skirt-reinforcement member 1930 are attached to the frame 1902 such that the skirt-reinforcement member 1930 has sufficient tension along its length to minimize radial movement of the skirt 1912 throughout the cardiac cycle.

In FIGS. 19 and 19A, the skirt-reinforcement member 1930 extends in a horizontal orientation over the side opening 1918 in a center or middle thereof. However, other placements of the skirt-reinforcement members are contemplated herein. For example, in the embodiment depicted in FIG. 19B, a skirt-reinforcement member 1930B extends in a vertical orientation over the side opening 1918 in a center or middle thereof. A first end 1932B of a skirt-reinforcement member 1930B is longitudinally offset from a second end 1934B of the skirt-reinforcement member 1930B such that the skirt-reinforcement member 1930B is parallel or substantially parallel relative to the axis LA of the frame. The first end 1932B of the skirt-reinforcement member 1930B is attached to a first crown 1920B defining the respective side opening 1918 and the second end 1934B of the skirt-reinforcement member 1930 is attached to a second or opposing crown 1920B defining the respective side opening 1918 such that the skirt-reinforcement member 1930B spans vertically across the side opening 1918.

Figure 19C:
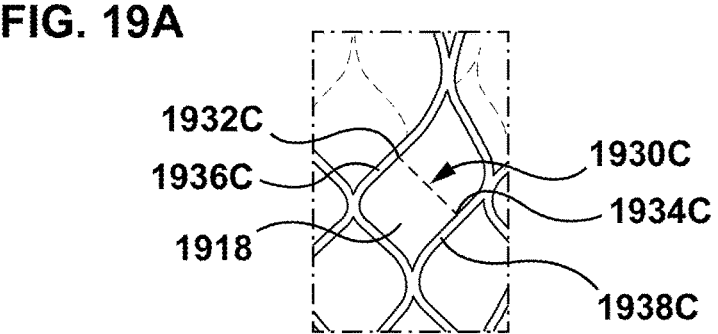
FIG. 19C is an enlarged view of a side opening of a docking prosthesis according to another embodiment hereof, wherein a skirt-reinforcement member extends in an angled orientation.

In another embodiment depicted in FIG. 19C, a first end 1932C of a skirt-reinforcement member 1930C is circumferentially offset from a second end 1934C of the skirt-reinforcement member 1930C such that the skirt-reinforcement member 1930C is angled relative to the axis LA of the frame. The first end 1932C of the skirt-reinforcement member 1930C is attached to a first edge 1936C defining the respective side opening 1918 and the second end 1934C of the skirt-reinforcement member 1930C is attached to a second or opposing edge 1938C defining the respective side opening 1918. Adjacent skirt-reinforcement members 1930C may have alternating orientations (i.e., diagonally downward and diagonally upward) such that the skirt-reinforcement members 1930C collectively circumscribe the frame in a zig-zag configuration. However, adjacent skirt-reinforcement members 1930C are not required to have alternating orientations and further each side opening 1918 is not required to include a skirt reinforcement member as described above.

Similar to the skirt-reinforcement members 1030, 1130, 1230 described above, the skirt-reinforcement members 1930, 1930B, 1930C may include a strip of fabric or tissue in addition to a filament or strand of suture that forms a plurality of stitches. In addition, an alternative to the plurality of skirt-reinforcement members 1930, the docking prosthesis 1900 may include a continuous band or ring that extends 360° around an outer surface of the frame 1902. The ring would be attached to the skirt 1912 and may be the same as the skirt-reinforcement member 1330 described above. The ring would be positioned over the same row of side openings 1918 as shown with respect to the skirt-reinforcement members 1930 in FIG. 19.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A prosthesis having a radially expanded configuration and a radially compressed configuration, the prosthesis comprising:
    a frame including a plurality of crowns and a plurality of struts with each crown being formed between a pair of opposing struts, wherein a plurality of side openings is defined by edges of the plurality of crowns and the plurality of struts;
    a skirt coupled to a surface of the frame, wherein the skirt extends over at least one side opening of the plurality of side openings of the frame;
    a prosthetic valve component including a plurality of leaflets disposed within and secured to the frame, the prosthetic valve being configured to block blood flow in one direction to regulate blood flow through a central lumen of the frame, wherein a margin of attachment is formed at the junction of the leaflets to the skirt; and
    a skirt-reinforcement member that spans the at least one side opening of the plurality of side openings of the frame from a first crown or strut edge defining the at least one side opening to a second crown or strut edge defining the at least one side opening, wherein the skirt-reinforcement member is longitudinally spaced apart from the margin of attachment, the skirt-reinforcement member having a first end, a second end, and a length therebetween, wherein the first end of the skirt-reinforcement member is attached to the first crown or strut edge and the second end of the skirt-reinforcement member is attached to the second crown or strut edge, and wherein the skirt-reinforcement member is attached to the skirt along an unsupported portion of the skirt that spans the at least one side opening.

2. The prosthesis of claim 1, wherein the skirt-reinforcement member includes a suture forming a plurality of stitches.

3. The prosthesis of claim 1, wherein the skirt-reinforcement member includes tissue.

4. The prosthesis of claim 1, wherein the skirt-reinforcement member includes fabric.

5. The prosthesis of claim 1, wherein an end of the frame includes a row of side openings around a circumference of the frame, the row including between six and nine side openings.

6. The prosthesis of claim 1, wherein the first end of the skirt-reinforcement member is circumferentially offset from the second end of the skirt-reinforcement member such that the skirt-reinforcement member is angled relative to an axis of the frame.

7. The prosthesis of claim 1, wherein the first end of the skirt-reinforcement member is circumferentially aligned with the second end of the skirt-reinforcement member such that the skirt-reinforcement member extends substantially perpendicular relative to an axis of the frame.

8. The prosthesis of claim 7, wherein the at least one side opening includes a maximum width and the skirt-reinforcement member spans across the at least one side opening at the maximum width.

9. The prosthesis of claim 7, wherein the frame includes a plurality of nodes, each node being a region where two of the plurality of crowns of the frame meet, and wherein the skirt-reinforcement member spans across the at least one side opening from one node to another node.

10. The prosthesis of claim 1, wherein the frame includes a row of side openings around a circumference of the frame and a skirt-reinforcement member spans each side opening of the row of side openings around the circumference of the frame.

11. The prosthesis of claim 1, wherein the frame is an inner frame and the prosthesis further comprises an outer frame coupled to the inner frame, the outer frame having a greater diameter than the inner frame.

12. The prosthesis of claim 1, wherein the prosthesis is a heart-valve prosthesis and the skirt-reinforcement member is positioned downstream of the margin of attachment.

13. The prosthesis of claim 12, wherein the heart-valve prosthesis is configured for placement within a mitral valve in situ.

14. A prosthesis having a radially expanded configuration and a radially compressed configuration, the prosthesis comprising:
a frame including a plurality of crowns and a plurality of struts with each crown being formed between a pair of opposing struts, wherein a plurality of side openings is defined by edges of the plurality of crowns and the plurality of struts;
a skirt coupled to a surface of the frame, wherein the skirt extends over at least one side opening of the plurality of side openings of the frame;
a prosthetic valve component including a plurality of leaflets disposed within and secured to the frame, the prosthetic valve being configured to block blood flow in one direction to regulate blood flow through a central lumen of the frame, wherein a margin of attachment is formed at the junction of the leaflets to the skirt; and
a skirt-reinforcement member that circumscribes an outer surface of the frame, wherein at least a portion of the skirt-reinforcement member is longitudinally spaced apart from the margin of attachment, wherein skirt-reinforcement member is attached to the skirt along an unsupported portion of the skirt that spans the at least one side opening of the plurality of side openings of the frame and wherein the skirt-reinforcement member is not directly attached to the frame.

15. The prosthesis of claim 14, wherein the skirt-reinforcement member is a ring of an elastic material.

16. The prosthesis of claim 14, wherein the at least one side opening of the plurality of side openings is substantially diamond-shaped.

17. The prosthesis of claim 14, wherein an end of the frame includes a row of side openings around a circumference of the frame, the row including between six and nine side openings.

18. The prosthesis of claim 14, wherein the frame is an inner frame and the prosthesis further comprises an outer frame coupled to the inner frame, the outer frame having a greater diameter than the inner frame.

19. The prosthesis of claim 14, wherein the prosthesis is a heart-valve prosthesis and the skirt-reinforcement member is positioned downstream of the margin of attachment.

20. The prosthesis of claim 19, wherein the heart-valve prosthesis is configured for placement within a mitral valve in situ.

* * * * *